United States Patent [19]
Wei et al.

[11] Patent Number: 5,681,589
[45] Date of Patent: Oct. 28, 1997

[54] LIPOSOMAL CERAMIDE-RELATED LIPOSOMES AND THE THERAPEUTIC USE THEREOF

[75] Inventors: Yong Wei, Branchburg; Eric Mayhew, Monmouth Junction; Imran Ahmad, Plainsboro, all of N.J.; Andrew S. Janoff, Yardley, Pa.

[73] Assignee: The Lipsome Company, Inc., Princeton, N.J.

[21] Appl. No.: 545,164

[22] Filed: Oct. 19, 1995

Related U.S. Application Data

[60] Division of Ser. No. 383,291, Feb. 2, 1995, which is a continuation-in-part of Ser. No. 190,295, Feb. 2, 1994, abandoned.

[51] Int. Cl.$^6$ ................................................ A61K 9/127
[52] U.S. Cl. ................................ 424/450; 428/402.2
[58] Field of Search ........................ 424/450; 436/829; 428/402.2

[56] References Cited

U.S. PATENT DOCUMENTS

| | | | |
|---|---|---|---|
| 4,522,803 | 6/1985 | Lenk et al. | 424/1.1 |
| 4,588,578 | 5/1986 | Fountain et al. | 424/1.1 |
| 4,721,612 | 1/1988 | Janoff et al. | 424/1.21 |
| 4,975,282 | 12/1990 | Cullis et al. | 424/450 |
| 5,008,050 | 4/1991 | Cullis et al. | 264/4.3 |
| 5,030,453 | 7/1991 | Lenk et al. | 424/450 |
| 5,059,421 | 10/1991 | Loughrey et al. | 424/417 |
| 5,077,056 | 12/1991 | Bally et al. | 424/450 |
| 5,100,662 | 3/1992 | Bolcsak et al. | 424/88 |
| 5,169,637 | 12/1992 | Lenk et al. | 424/450 |
| 5,415,855 | 5/1995 | Critchley | 424/61 |

FOREIGN PATENT DOCUMENTS

| | | | |
|---|---|---|---|
| 92/03129 | 3/1992 | WIPO | A61K 31/13 |

OTHER PUBLICATIONS

Ohashi et al, Tetrahedron Letters 29, #10, pp. 1189–1192, 1988.

Bangham, et al., "Diffusion of Univalent Ions across the Lamellae of Swollen Phospholipids", J. Mol. Bio. 13:238–252, 1965.

Baringa, M.., "Death Gives Birth to the Nervous System. But How?", Science, 259, 762–763, 1993.

Cohen, J., "Overview: Mechanisms of apoptossis", Immunology Today, 14(3), 1993, 126–130.

Cohen, J. "Programmed Cell Death in the Immune System", Advances in Immunology, 50, 55–85, 1991.

Cullis, et al., in:*Liposomes, From Biophysics to Therapeutics* (M.J. Ostro ed.,), Marcel Dekker, pp. 39–72 (1987).

Dbaibo, et al., "Tumore Necrossis Factor $-\alpha$(TNF$-\alpha$) Signal Transduction through Ceramide", J. Biol. Chem. 268(24), 17762–17766, 1993.

(List continued on next page.)

*Primary Examiner*—Gollamudi S. Kishore
*Attorney, Agent, or Firm*—Kenneth B. Rubin

[57] ABSTRACT

This invention provides a compound having the formula $R^1$-$Y^1$—$CHZ^1$-$CH(NY^2Y^3)$—$CH_2$-$Z^2$, wherein: $R^1$ is a straight-chained alkyl, alkenyl or alkynyl group having from 8 to 19 carbon atoms in the aliphatic chain; $Y^1$ is —CH=CH—, —C≡C— or —CH(OH)CH(OH)—; $Z^1$ is OH or a conversion-inhibiting group; $Z^2$ is a conversion-inhibiting group; $Y^2$ is H, a phenyl group, an alkyl-substituted phenyl group having from 1 to about 6 carbons in the alkyl chain, or an alkyl chain having from 1 to 6 carbons; $Y^3$ is H or a group having the formula —C(O)$R^2$ or —S(O)$_2R^2$; $R^2$ is a straight-chained alkyl, alkenyl or alkynyl group having from 1 to 23 carbon atoms in the chain; and when $Z^2$ is an amino, $R^2$ is an aliphatic chain having from 1 to 9 or from 19 to 23 carbon atoms in the aliphatic chain.

15 Claims, 21 Drawing Sheets

OTHER PUBLICATIONS

Fesus, et al., "Apoptosis: molecular mechanisms in programmed cell death", European J. of Cell Biology, 56, 170–177, 1991.

Fishbein, et al., "Ceramide–mediated Growth Inhibition and CAPP are Conserved in *Saccharomyces cerevissiae*", J. biol Chem., 268(13), 9255–9261, 1993.

Gronberg, et al., "Interaction of Cholesterol with Synthetic Sphingomyelin Derivatives in Mixed Monolayers", Biochemistry, 1991, 30, 10746–10754.

Kabelitz, et al., "Activation–induced cell death (apoptosis) of mature peripheral T lymphocytes", Immunology Today, 14(7), 1993, 338–.

Kan et al., "Interaction of Cholesterol with Sphingomyelin in Bilayer membranes: Evidence that the Hydroxy Group of Sphingomyelin Does Not Modulate the Rate of Cholesterol Exchange between Vesicles", Biochemistry, 1991, 30, 7759–7766.

Kim, et al., "Identification of Sphingomyelin Turnover as an Effector Mechanism for the Action of Tumor Necrosis Factor α and γ–Interferon", J. Biol. Chem. 266(1), 484–489, 1991.

Kolesnick, R., "Ceramide: a novel second messenger", Trends in Cell Biology, 2, 1992, 232–236.

Martin, S., "Apoptosis: suicide, execution or murder?", Cell Biology Trends,.

Marx, J., "Cell Death Studies Yield Cancer Clues", Science, 259: 760–1 (1993).

Morishige, et al., "In vitro cytostatic effect of TNF (Tumore Necrosis Factor) entrapped in immunoliposomes on cells normally insecsitive to TNF", BBA, 1151 (1993) 59–68.

Obeid, et al., "Programmed Cell Death Induced By Ceramide", Science, 259, 1769–1771, 1993.

Ohashi, et al., "Synthesis of Phophonophingoglycolipid Found in Marine Snail Turbo Cornutus", Tetrahedron Letters, 29(10): 1189–1192, 1988.

Papahadjopoulos et al.., "Phospholipid Model Membranes, I. Structural Characteristic of Hydrated Liquid Crystals", Biochim. Biophys Acta 1967; 135:624–638.

Raines, et al., "Sphingomyelinase and Ceramide Activate Mitogen–activated Protein Kinase in Myeloid HL–60 Cells", J. Biol. Chem., 268(20), 14572–14575, 1993.

Stedman's Medical Dictionary (Illustrated), (24th edition J. V. Basmajian et al., eds.) Williams and Wilkins, Baltimore, MD, 1982, p. 99.

Sugimoto, et al., "Preparation of sphingosine derivatives as antitumor agents", Chemical Abstracts, 1990, 112:566573n.

Vilcek, et al., "Tumor Necrosis Factor, New Insights into the Molecular Mechanissms of its Multiple Actions", J. Biol. Chem., 266(12), 7313–7316, 1991.

Williams, et al., "Apoptosis: final control point in cell biology", Trends in Cell Biology, 2, 263–267, 1992.

Williams, et al., "Molecular Regulation of Apoptosis: Genetic Controls on Cell Death", Cell, 74, 777–779, 1993.

Lukevics, E., "Biological Activity of nitrogen–containing organosilicon compounds", Nobel Symp. 1977 (pub. 1978) Biochem. Silicon, Relat. Probl., 40, 435–437.

Fig. 2a
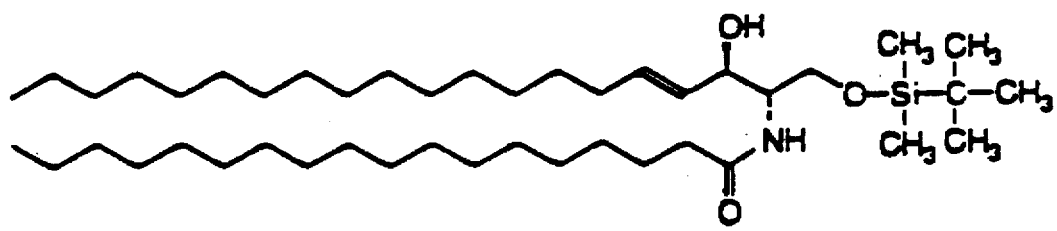
Type III Cer-1-TBDMS
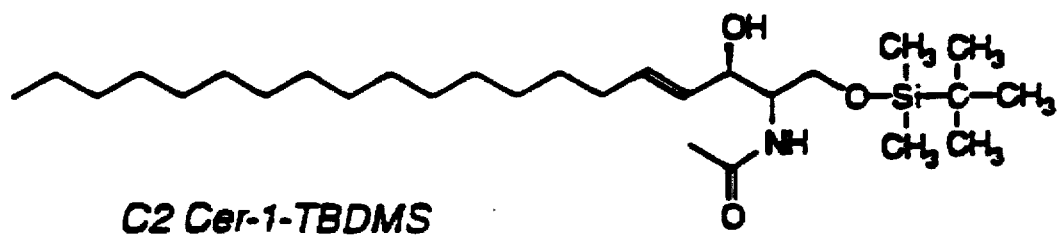
C2 Cer-1-TBDMS
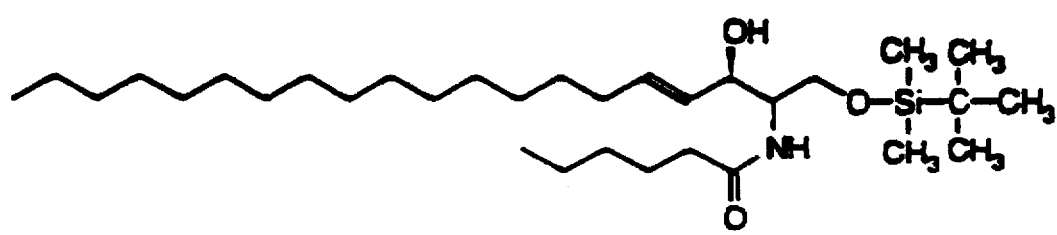
C6 Cer-1-TBDMS
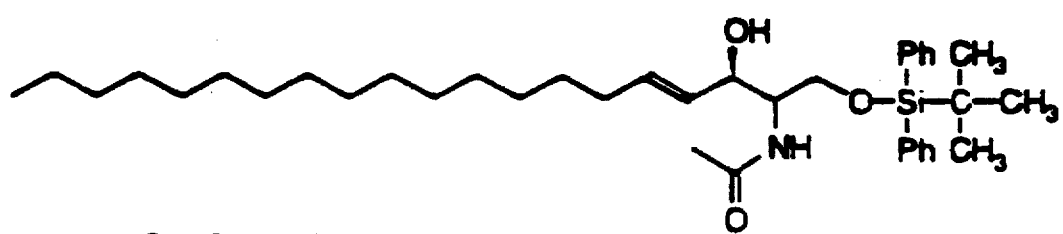
C2 Cer-1-TBDPS 1-Acetate-3-one C6-Cer 4,5-Diol C6-Cer

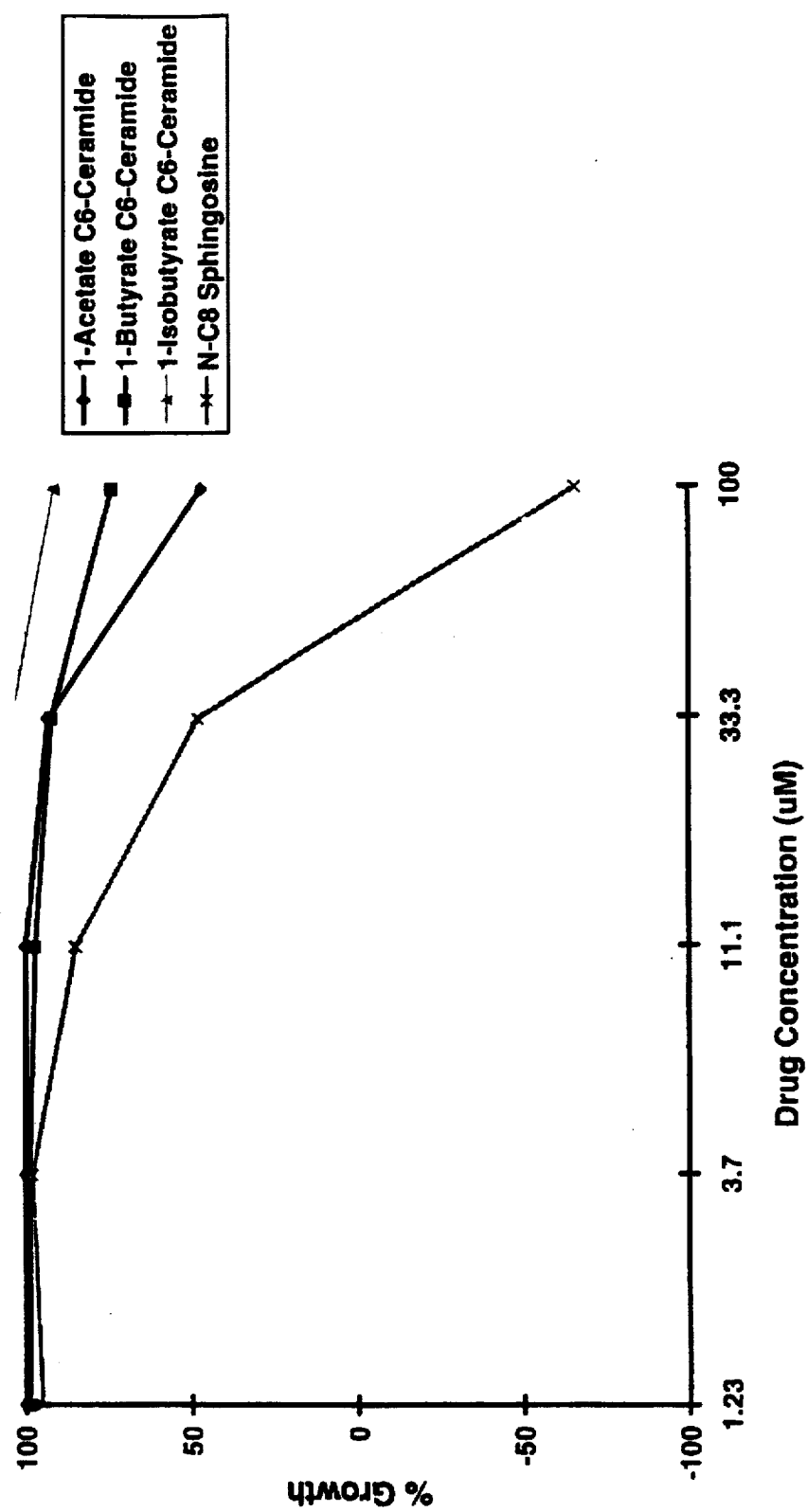

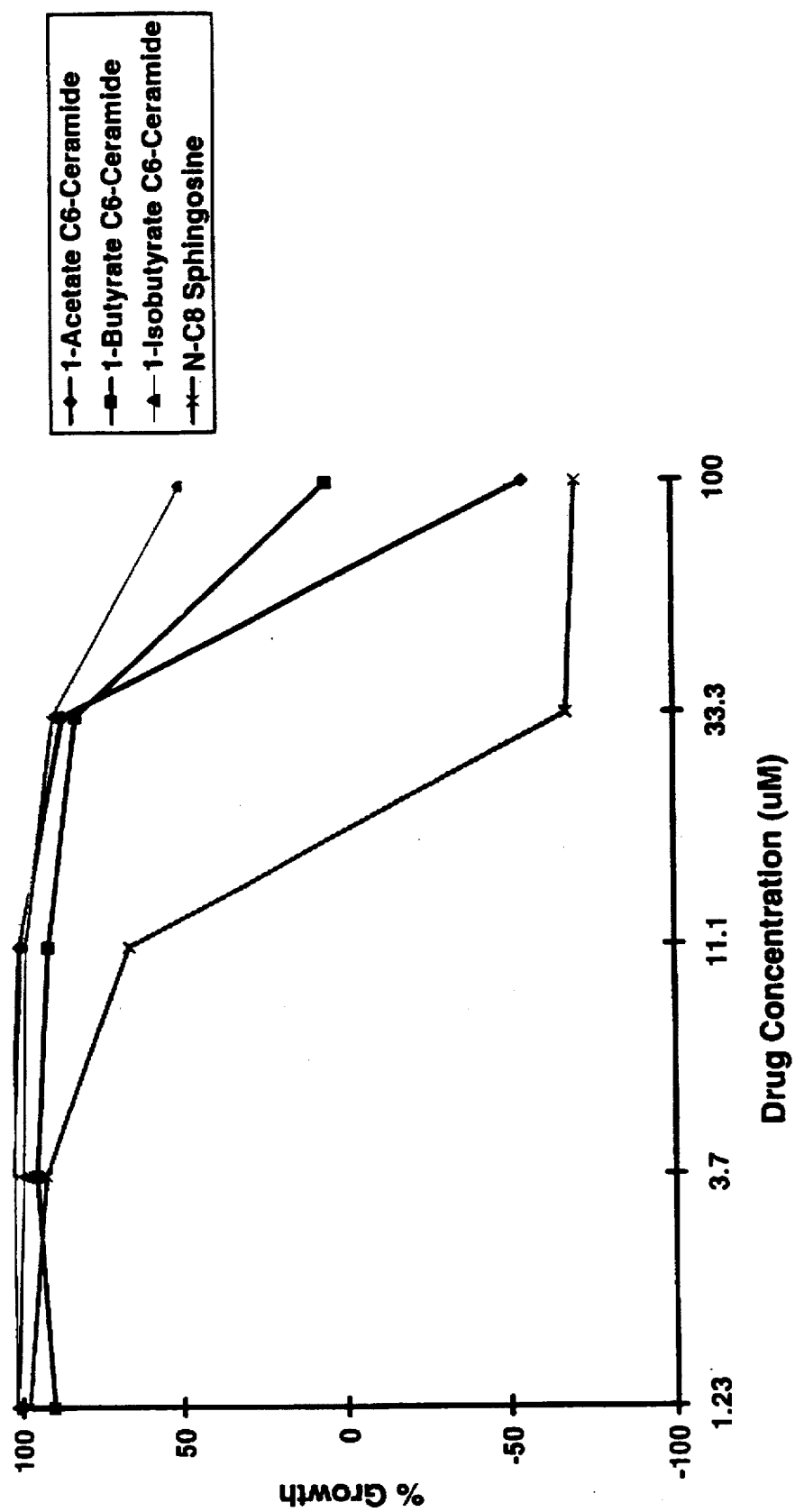

*In Vitro* Sensitivity of A549 to C6-Ceramide Derivatives After Eight Hour Drug Exposure

*In Vitro* Sensitivity of A549 to C6-Ceramide Derivatives After 48 Hour Drug Exposure

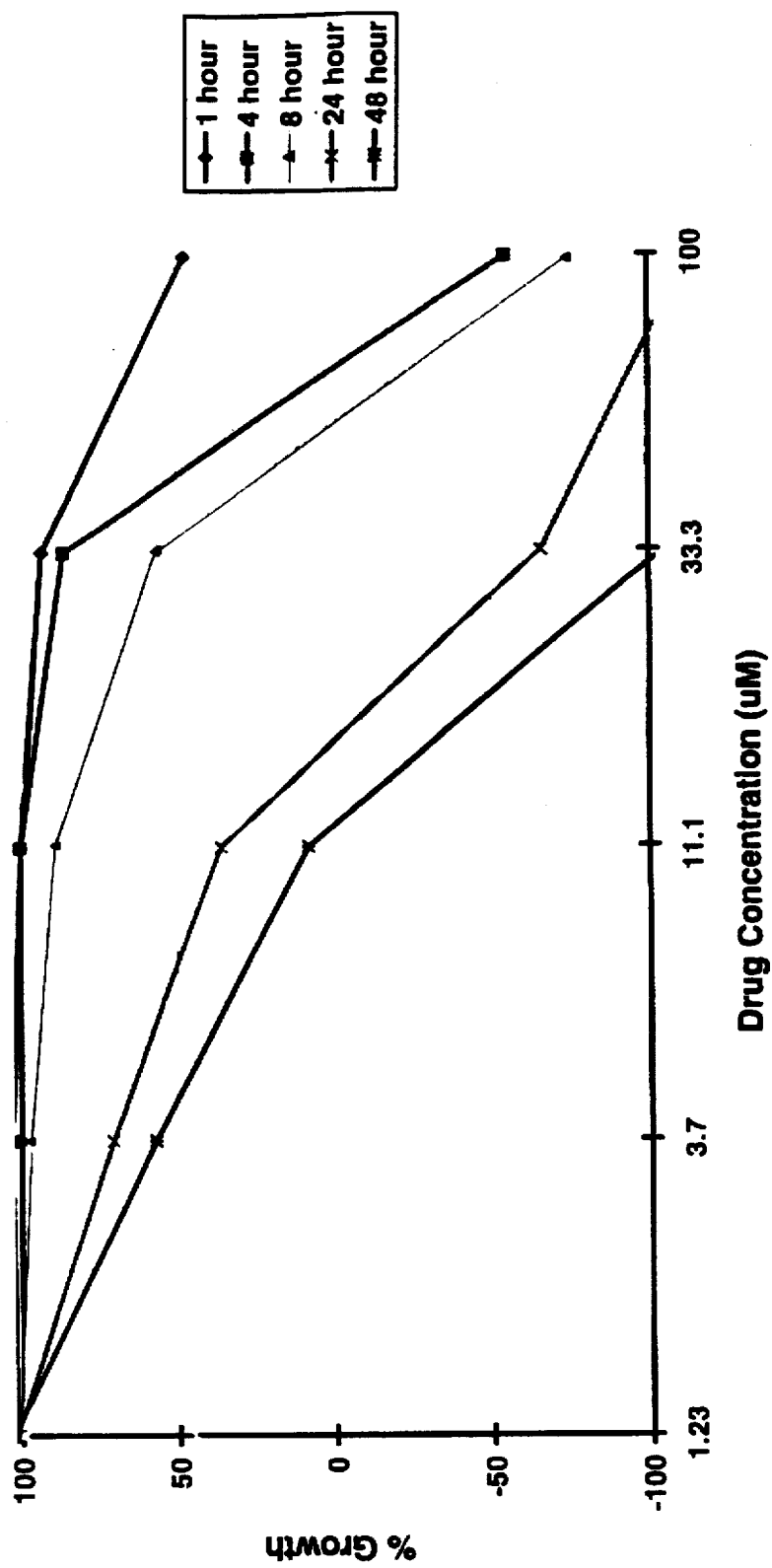
Fig. 10 *In Vitro* Sensitivity of A549 to 1-Acetate C6-Ceramide at Different Exposure Times

*In Vitro* Sensitivity of A549 to 1-Isobutyrate C6-Ceramide at Different Exposure Times

LIPOSOMAL CERAMIDE-RELATED LIPOSOMES AND THE THERAPEUTIC USE THEREOF

This application is a division of U.S. Ser. No. 08/383,291 pending, filed Feb. 2, 1995, which is a continuation-in-part of U.S. Ser. No. 08/190,295, filed Feb. 2, 1994 now abandoned.

FIELD OF THE INVENTION

This invention is directed to pharmaceutically active sphingolipid compounds, to liposomes containing pharmaceutically active sphingolipid compounds, and to methods of using such compounds and liposomes, particularly for the treatment of animals afflicted with cancers.

Cell death in multicellular organisms can be an accidental response to external trauma, or it can be a programmed response to internal or external stimuli. Necrosis, or accidental cell death, is most often seen when cells die uncontrollably as a result of sudden and severe injury to an organism, e.g., by physical or chemical trauma, sustained hyperthermia or ischemia (see, e.g., J. Cohen, Immunol. Today. 14(3):126 (1993)); J. Marx, Science 259: 750 (1993) ). Plasma membrane damage can cause cells to lose their ability to regulate their osmotic pressure, and cell rupture can thereby result. The consequent leakage of cell contents can cause further injury to surrounding cells and can invoke an inflammatory response to clear away the cellular debris.

Apoptosis, by contrast, describes a programmed series of events resulting in cell death by fragmentation into membrane-bound particles; these particles are then phagocytosed by other cells (see, e.g., Stedman's Medical Dictionary (Illustrated), supra). Cells typically undergo apoptosis in physiologically determined circumstances such as the elimination of self-reactive T cells, the death of cells (e.g., neutrophils) with short half-lives, involution of growth factor-deprived cells, morphogenetic cell death during embryonic development and the deaths of cellular targets of cell-mediated cytotoxicity (see, e.g., J. Cohen, supra).

Cells undergoing apoptosis can break up into apoptotic bodies, which are cellular fragments that retain their membranes and are able to regulate their osmotic pressures. Unlike necrotic cells, there is usually no leakage of cellular contents and hence, no invocation of an inflammatory response. Apoptotic cells typically have disrupted plasma membranes and condensed, disrupted nuclei. Nuclear chromatin in these cells is fragmented randomly between nucleosomes, as the result of endonuclease activation during apoptosis.

Although transcription in apoptotic cells ceases, cell death occurs more rapidly than would be expected from the cessation of transcription alone. This indicates that cellular processes in addition to transcription termination are likely to be involved in apoptosis. Gene expression itself may actually be required for the occurrence of the morphological changes associated with apoptosis (see, e.g., J. Cohen, supra). Alternatively, inhibition of transcription termination may itself induce apoptosis. Furthermore, apoptosis of some cells does not appear to be affected one way or the other by the inhibition of protein synthesis. Expression of the bcl-2 oncogene, for example, can inhibit the apoptosis otherwise induced by different stimuli, and may thereby contribute to cancer development. Accordingly, inhibition of bcl-2 expression may be required to induce apoptosis (see, e.g., J. Marx, supra; J. Cohen, supra; G. Williams and C. Smith, Cell 74:777 (1993); M. Barinaga, Science 259: 762 (Feb. 5, 1993)). C-myc protein is known to stimulate cell proliferation; however, it may also stimulate apoptosis in the absence of additional proliferative stimuli. p53, which is thought to suppress tumor growth, may also stimulate apoptosis. C-fas, a transmembrane protein homologous to Tumor Necrosis Factor (TNF), can also induce apoptosis, as can TNF itself.

TNF is a monokine protein produced by monocytes and macrophages. There are two known structurally and functionally related TNF proteins, TNF-α and TNF-β, both of which bind to the same cell surface receptors. Binding to these receptors by TNF leads to the activation of multiple signal transduction pathways, including the activation of sphingomyelinase (see, e.g., M. Raines et al., J. Biol. Chem. 268(20):14572 (1993); L. Obeid et al., Science 259:1769 (Mar. 12, 1993); H. Morishige et al., Biochem. Biophys. Acta. 1151:59 (1993); J. Vilcek and T. Lee, J. Biol. Chem. 266(12):7313 (1991); Dbaibo et al., J. Biol. Chem. 268(24):17762 (1993); R. Kolesnik, Trends Cell. Biol. 2:232 (1992); J. Fishbein et al., J. Biol. Chem. 268(13):9255 (1993)).

Applicants have found that increases in ceramide concentrations can stimulate apoptosis. Ceramides are a class of sphingolipids comprising fatty acid derivatives of a sphingoid, e.g., sphingosine, base (see, e.g., Stedman's Medical Dictionary (Illustrated), 24th edition (J. V. Basmajian et al., eds.), Williams and Wilkins, Baltimore (1982), p. 99)). Different ceramides are characterized by different fatty acids linked to the sphingoid base. For example, stearic acid can be attached to the amide group of sphingosine to give rise to the ceramide $CH_3(CH_2)_{12}CH=CH-CHOH-CH(CH_2OH)-NH-CO-(CH_2)_{16}CH_3$. Shorter- or longer-chain fatty acids can also be linked to the sphingoid base. Applicants have also found that attachment of certain chemical groups to sphongolipids and ceramides so as to form analogs of such compounds can inhibit bioconversion of ceramides to sphingomyelins, and can thereby lead to an apoptosis stimulating increase in ceramide concentrations.

Ceramides are found in all eukaryotic cell membranes, and are known to participate in a variety of critical cellular processes. Furthermore, certain sphingolipid compounds have been found to play a role in prevention of cellular proliferation ( ). However, none of these references teach applicants' chemical compounds and liposomes, or their use in stimulating cell death.

SUMMARY OF THE INVENTION

Provided herein is a compound having the formula $R^1-Y^1-CHZ^1-CH(NY^2Y^3)-CH_2-Z^2$, wherein: $R^1$ is a straight-chained alkyl, alkenyl or alkynyl group having from 8 to 19 carbon atoms in the aliphatic chain; $Y^1$ is —CH=CH—, —C≡C— or —CH(OH)CH(OH)—; $Z^1$ is OH or a conversion-inhibiting group; $Z^2$ is a conversion-inhibiting group; $Y^2$ is H, a phenyl group, an alkyl-substituted phenyl group having from 1 to about 6 carbons in the alkyl chain, or an alkyl chain having from 1 to 6 carbons; $Y^3$ is H or a group having the formula —C(O)R² or —S(O)₂R²; $R^2$ is a straight-chained alkyl, alkenyl or alkynyl group having from 1 to 23 carbon atoms in the chain; and wherein when $Z^2$ is an amino, $R^2$ is an aliphatic chain having from 1 to 9 or from 19 to 23 carbon atoms in the aliphatic chain. Preferably, $R^1$ is an alkyl group, more preferably, $CH_3(CH_2)_{12}$—, $Y^1$ is —CH=CH—, $Y^2$ is H, $Y^3$ is —C(O)R² and $R^2$ is an alkyl chain.

Conversion-inhibiting groups can have the formula -X²X³ or —O—X²X³, wherein $X^2$ is selected from the group consisting of $CH_2$—, $C(CH_3)_2$—, $Si(PO_4)_2$—, $Si(CH_3)_2$—, $SiCH_3PO_4$—, $C(O)$— and $S(O)_2$— and wherein $X^3$ is selected from the group consisting of —C(O)H, —CO$_2$H, —CH$_3$, —C(CH$_3$)$_3$, —Si(CH$_3$)$_3$, —SiCH$_3$(C(CH$_3$)$_3$)$_2$, —Si(C(CH$_3$)$_3$)$_3$, —Si(PO$_4$)$_2$C(CH$_3$)$_3$, a phenyl group, an alkyl-substituted phenyl group having from 1 to 6 carbons in the alkyl chain, an alkyl chain having from 1 to 6 carbons, an amino moiety, a chlorine, a flourine, or a group having the formula C(R$^3$R$^4$)OH; each of R$^3$ and R$^4$ is independently an alkyl chain having from 1 to 6 carbons, a phenyl group or an alkyl-substituted phenyl group having from 1 to 6 carbons in the alkyl chain. Preferably, the conversion-inhibiting group is —OC(O)CH$_3$, —OC(O)CH$_2$CH$_2$CH$_3$, —OC(O)CH(CH$_3$)CH$_3$, or —OSi(CH$_3$)$_2$C(CH$_3$)$_3$, more preferably, —OSi(CH$_3$)$_2$C(CH$_3$)$_3$. Conversion-inhibiting groups can also have the formula -X$^1$ or —OX$^1$, wherein X$^1$ is C(O)H, CO$_2$H, CH$_3$, C(CH$_3$)$_3$, Si(CH$_3$)$_3$, SiCH$_3$(C(CH$_3$)$_3$)$_2$, Si(C(CH$_3$)$_3$)$_3$, Si(PO$_4$)$_2$C(CH$_3$)$_3$, a phenyl group, an alkyl-substituted phenyl group having from 1 to 6 carbons in the alkyl chain, an alkyl chain having from 1 to 6 carbons, an amino moiety, a flourine, a chlorine, or a group having the formula C(R$^3$R$^4$)OH, and each of R$^3$ and R$^4$ is independently an alkyl chain having from 1 to 6 carbons.

Preferably, the compound of this invention has the formula CH$_3$(CH$_2$)$_{12}$—CH=CH—CH$_2$Z$^1$-CH(NHY$^3$)—CH$_2$-Z$^2$. Y$^3$ is then a group having the formula —C(O)R$^2$, more preferably, —C(O)(CH$_2$)$_4$CH$_3$. Z$^2$ is preferably —OSi(CH$_3$)$_2$C(CH$_3$)$_3$, OSi(PO$_4$)$_2$C(CH$_3$)$_3$, —C(O)CH$_3$ or —OC(O)CH$_2$CH$_2$CH$_3$.

Also provided herein is a pharmaceutical composition comprising the compound of this invention and a pharmaceutically acceptable carrier; the composition can also comprise an additional bioactive agent. Further provided is a method of administering a bioactive compound to an animal, preferably a human, which comprises administering to the animal this composition; the method can comprise administering an additional bioactive agent to the animal.

The animal can be afflicted with a cancer, wherein the method comprises administering an amount of the composition which comprises an anticancer effective amount of the compound. Typically, the anticancer effective amount of the compound is at least about 0.1 mg of the compound per kg of body weight of the animal. Generally, the anticancer effective amount is from about 1 mg per kg to about 50 mg per kg. Treatable cancers include, without limitation, brain, breast, lung, ovarian, colon, stomach or prostate cancers, and can be sarcomas, carcinomas, neuroblastomas, or gliomas. Drug resistant cancers can also be treated.

Provided herein is a liposome having a bilayer which comprises a lipid and a compound having the formula R$^1$-Y$^1$—CHZ$^1$-CH(NY$^2$Y$^3$)—CH$_2$-Z$^2$, wherein: R$^1$ is a straight-chained alkyl, alkenyl or alkynyl group having from 5 to 19 carbon atoms in the chain; Y$^1$ is —CH=CH—, —C≡C— or —CH(OH)CH(OH)—; each of Z$^1$ and Z$^2$ is independently OH or a conversion-inhibiting group; Y$^2$ is H, a phenyl group, an alkyl-substituted phenyl group having from 1 to 6 carbons or an alkyl chain having from 1 to 6 carbons; Y$^3$ is H or a group having the formula -R$^2$, —C(O)R$^2$ or —S(O)$_2$R$^2$; R$^2$ is a straight-chained alkyl, alkenyl or alkynyl group having from 1 to 23 carbon atoms; and wherein the bilayer comprises at least about five mole percent of the compound. Y$^3$ is preferably R$^2$, which is preferably, —(CH$_2$)$_3$CH$_3$, —(CH$_2$)$_5$CH$_3$, —(CH$_2$)$_7$CH$_3$, or —(CH$_2$)$_9$CH$_3$, and more preferably, R$^2$ is —(CH$_2$)$_5$CH$_3$, or —C(O)R$^2$, which is preferably —C(O)(CH$_2$)$_4$CH$_3$. Preferably in the liposome of this invention, at least one of Z$^1$ and Z$^2$ is a conversion-inhibiting group, such as —OC(O)CH$_3$, —OC(O)CH$_2$CH$_2$CH$_3$, —OC(O)CH(CH$_3$)CH$_3$, or —OSi(CH$_3$)$_2$C(CH$_3$)$_3$. More preferably, the conversion-inhibiting group is —OSi(CH$_3$)$_2$C(CH$_3$)$_3$. Most preferably, the liposome comprises a compound having the formula CH$_3$—(CH$_2$)$_{12}$—CH=CH—CH$_2$Z$^1$-CH(NHY$^3$)—CH$_2$Z$^2$.

Preferably, the liposomal bilayer comprises at least about 10 mole percent of the compound. The bilayer can comprise vitamin D$_3$; such bilayers preferably comprise about 1 mole percent of vitamin D$_3$. The bilayer can also comprise a headgroup-modified lipid. The liposome can comprise an additional bioactive agent, and can be dehydrated.

Also provided herein is a pharmaceutical composition comprising the liposome of this invention and a pharmaceutically acceptable carrier. Further provided is a method of administering a compound to an animal which comprises administering to the animal the composition. The method can be used to treat an animal afflicted with a cancer, wherein a dose of the composition is administered and wherein the dose comprises an anticancer effective amount of the liposome. Typically, the dose comprises at least about 1 mg of the liposome per kg of body weight of the animal. Generally, the dose comprises from about 1 mg per kg to about 1000 mg per kg.

Provided herein is a liposome having a bilayer which comprises a lipid and a compound having the formula R$^1$-Y$^1$—CHZ$^1$-CH(NY$^2$Y$^3$)—CH$_2$-Z$^2$, wherein: R$^1$ is a straight-chained alkyl, alkenyl or alkynyl group having from 5 to 19 carbon atoms in the chain; Y$^1$ is —CH=CH—, —C≡C— or —CH(OH)CH(OH)—; each of Z$^1$ and Z$^2$ is independently OH or a conversion-inhibiting group; Y$^2$ is H, a phenyl group, an alkyl-substituted phenyl group having from 1 to 6 carbons or an alkyl chain having from 1 to 6 carbons; Y$^3$ is H or a group having the formula -R$^2$, —C(O)R$^2$ or —S(O)$_2$R$^2$; R$^2$ is a straight-chained alkyl, alkenyl or alkynyl group having from 1 to 23 carbon atoms; and wherein the bilayer comprises an anticancer-effective amount of the compound. Also provided is a pharmaceutical composition comprising this liposome and a pharmaceutically acceptable carrier. Further provided is a method of treating an animal afflicted with a cancer which comprises administering to the animal this composition.

BRIEF DESCRIPTION OF THE DRAWINGS

FIGS. 2A–2D: Ceramides Comprising Conversion-inhibiting Group. A: Type III Cer-1-TBDMS; C2 Cer-1-TBDMS; C6 Cer-1-TBDMS; C2 Cer-1-TBDPS. B: 3-TBDMS C6-Cer; 1-TBDMS C6-Cer; 1,3 DiTBDMS C6 Cer (YWI51.a); 1-TBDMS, 3-acetate C6-Cer; 1-TBDMS, 3-butyrate, C6-Cer. C: 1-acetate-3-one C6-Cer; 4,5-diol C6-Cer. D: N-C4 sphingosine; n-hexyl sphingosine; n-C8 sphingosine; N-C10 sphingosine.

Figure 5:
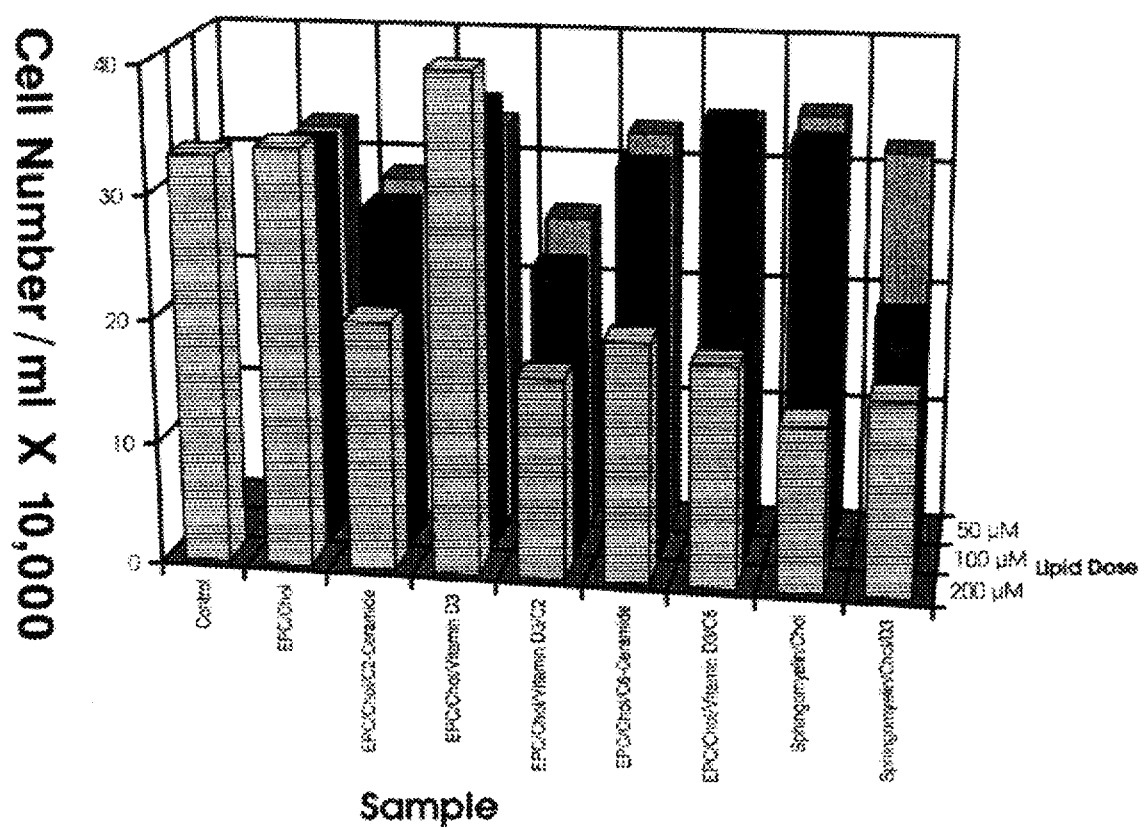

FIG. 5. Effect of Various Liposomal Ceramide/Sphingomyelin Formulations on the Growth of U937 Cells. The number of viable cells (per ml×10,000, y-axis) was determined for lipid doses of 50 µM, 100 µM and 200 µM (z-axis). X-axis: control, egg phosphatidylcholine/cholesterol (EPC/Chol), EPC/Chol/C2-ceramide (C2), EPC/Chol/vitamin D3 (D3), EPC/Chol/D3/C2, EPC/Chol/C6-ceramide (C6), EPC/Chol/D3/C6, Sphingomyelin (SM)/Chol and SM/Chol/D3 liposomes.

Figure 6:
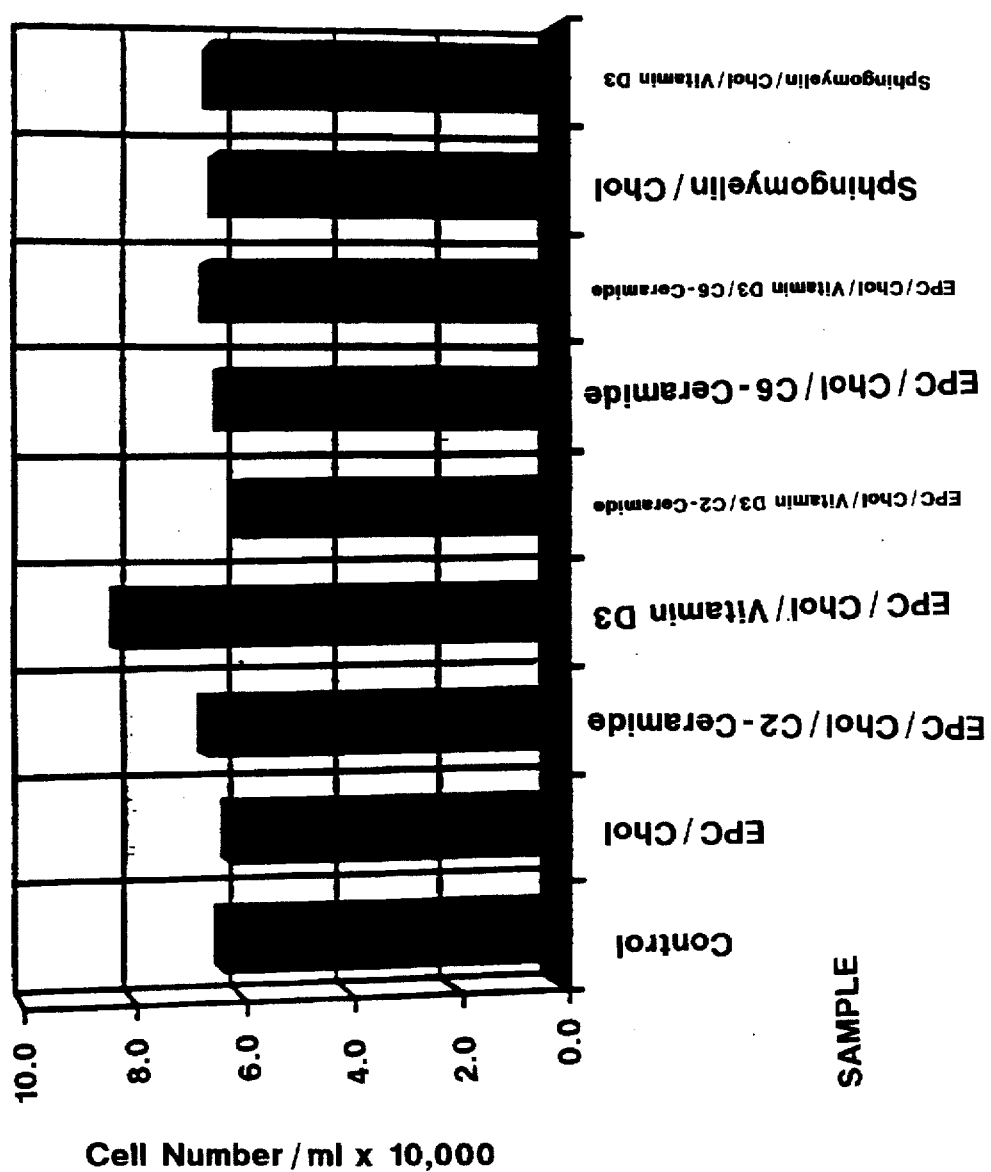

FIG. 6. Effect of Various Liposomal Ceramide/Sphingomyelin Formulations on the Growth of RPMI-7666 Cells. The number of viable cells (per ml×10,000, y-axis) was determined for a lipid dose of 200 µM. X-axis: control, egg phosphatidylcholine/cholesterol (EPC/Chol), EPC/Chol/C2-ceramide (C2), EPC/Chol/vitamin D3 (D3), EPC/Chol/D3/C2, EPC/Chol/C6-ceramide (C6), EPC/Chol/D3/C6, Sphingomyelin (SM)/Chol and SM/Chol/D3 liposomes.

Figure 7:
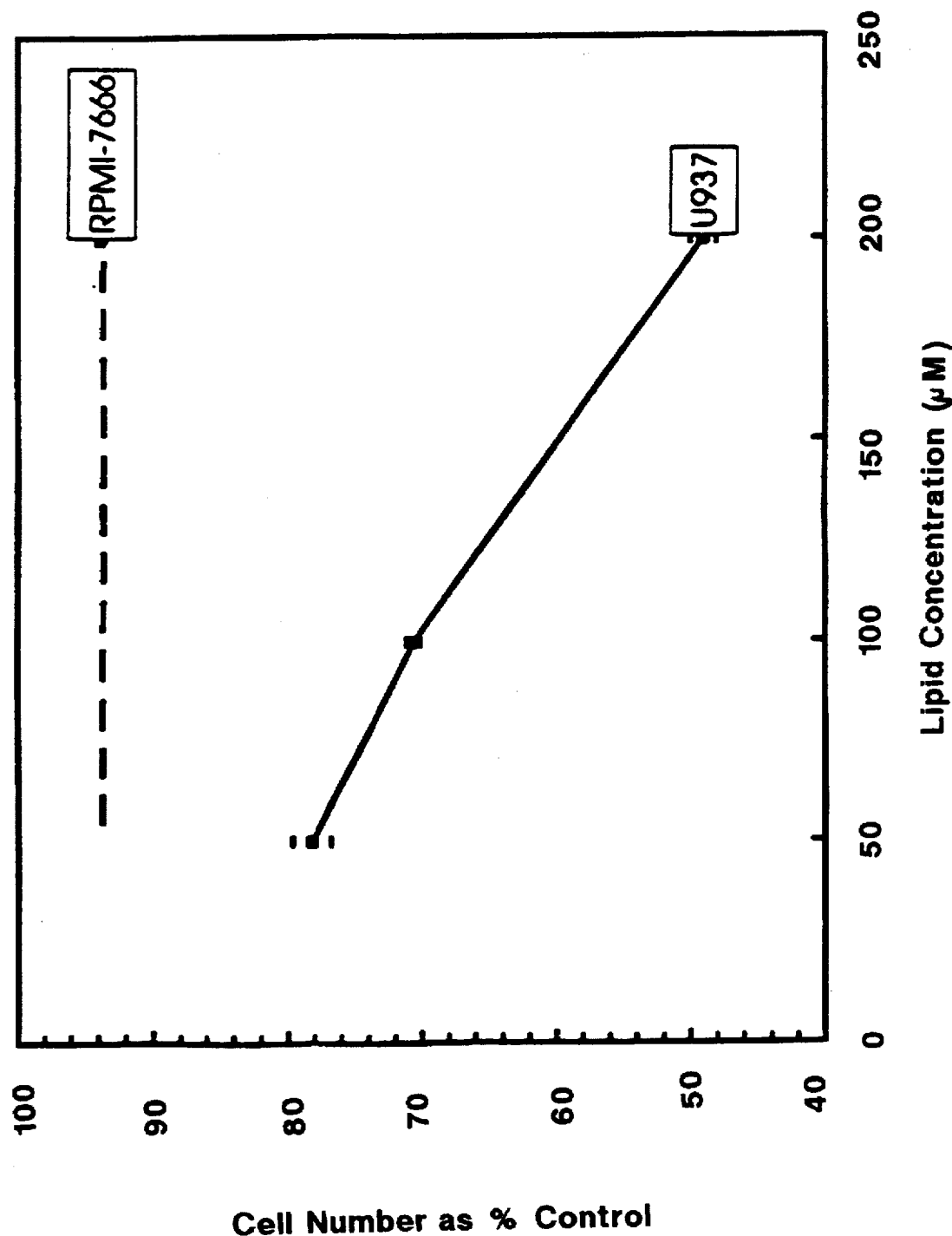

FIG. 7. Effect of Liposomal Ceramide on the Growth of Normal (RPMI-7666) and Cancer (U-937) Cells. The number of viable cells in each of the cultures was determined and is given as the percent relative to the control (y-axis).

Figure 8:
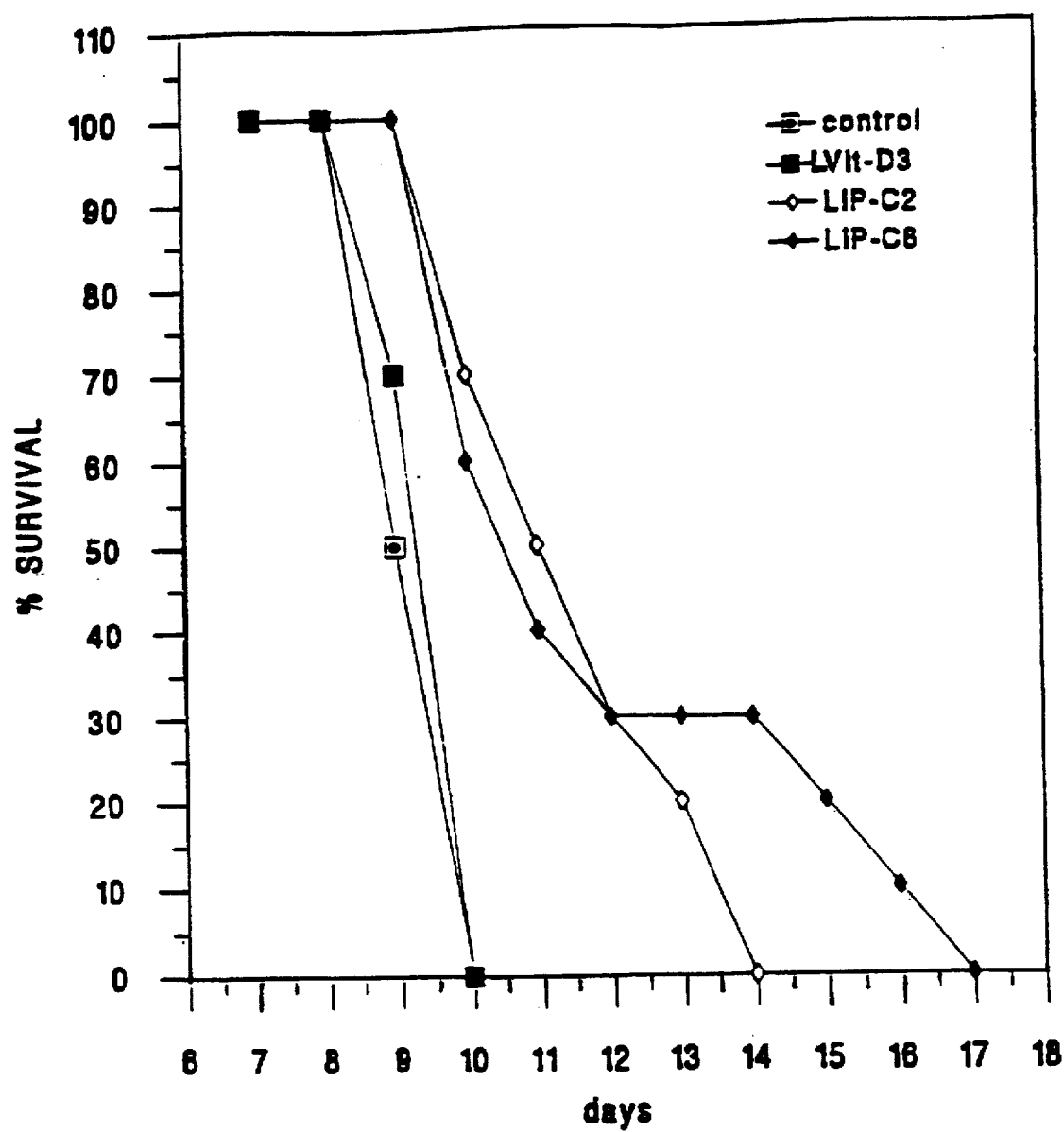
Figure 9C:
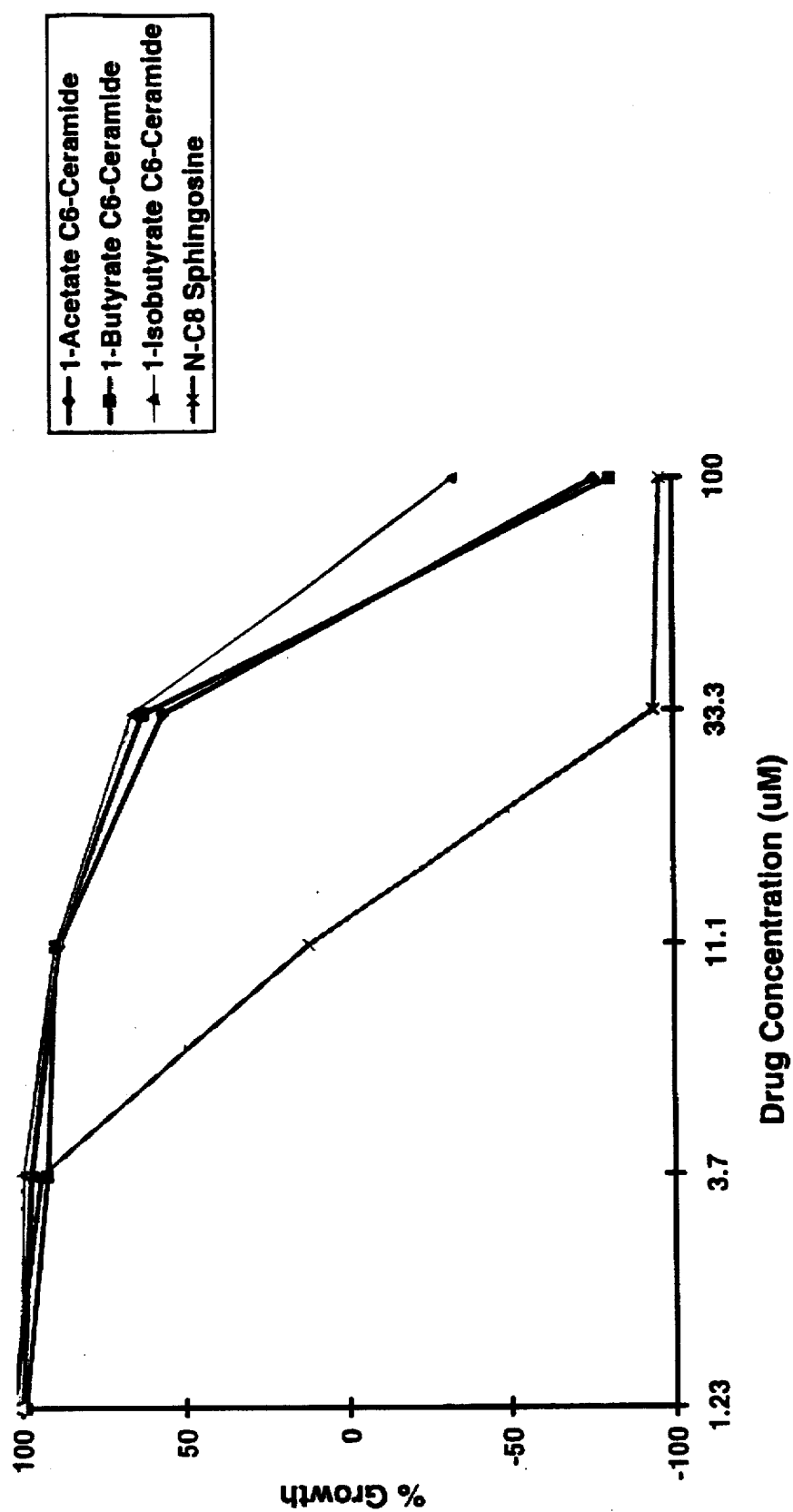
Figure 9D:
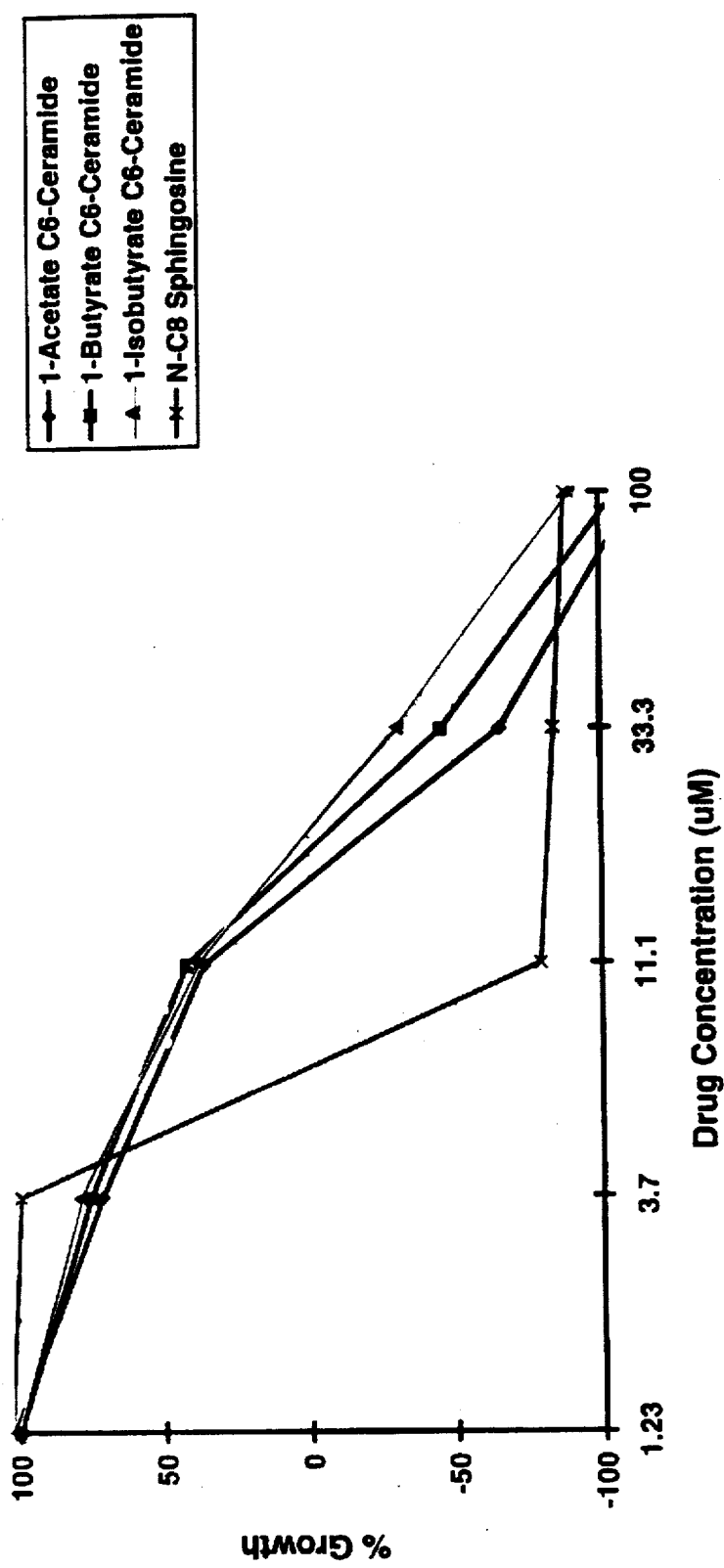
Figure 9E:
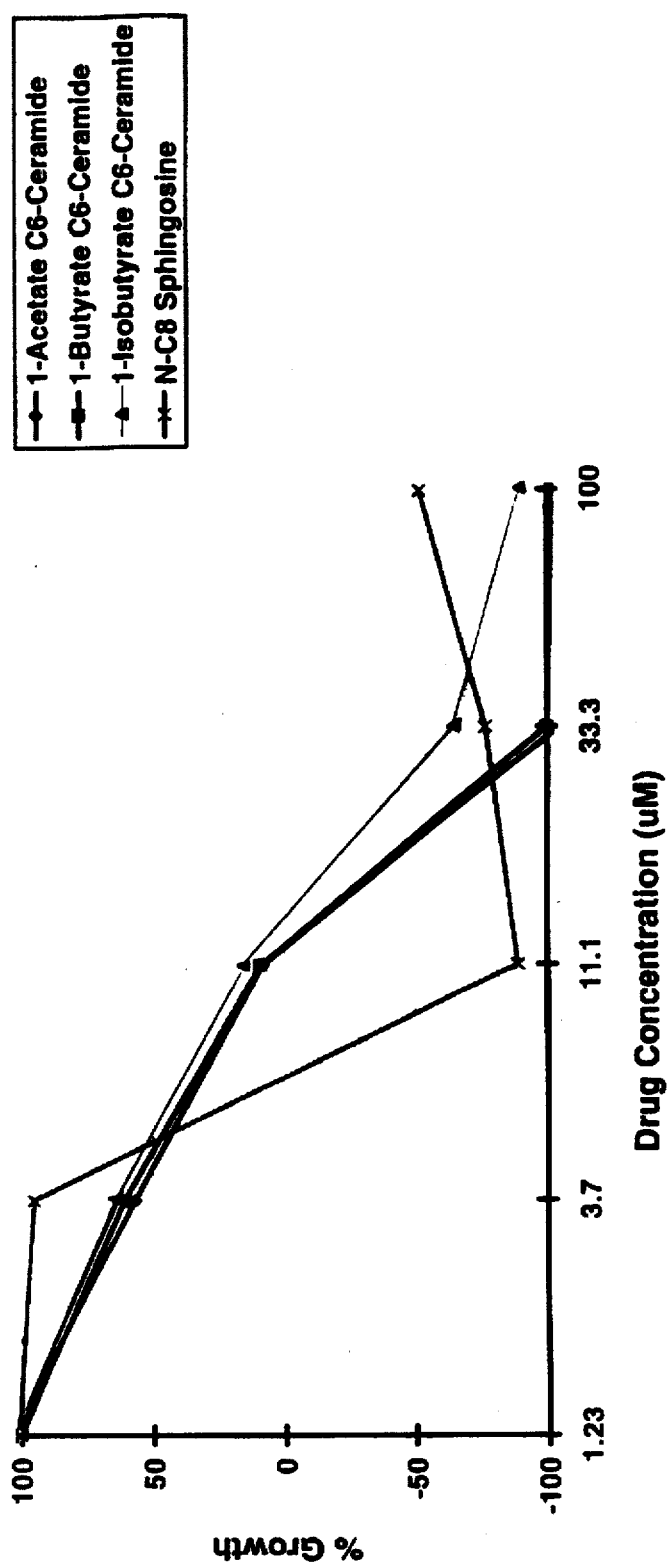

FIG. 8. Therapeutic Efficacy of Liposomal Ceramides in Mice. X-axis: days post-liposome/control administration; y-axis: percent survival in treatment group. Circle-in-square: control mice administered HEPES buffered saline; filled square: liposomal vitamin D3; open diamond: liposomal C2 ceramide; filled diamond: liposomal C6 ceramide.

FIGS. 9A–9E: In Vitro Sensitivity of A549 Cells to C6-Ceramide Derivatives. A: one-hour exposure; B: four-hour exposure; C: eight-hour exposure; D: twenty four-jour exposure; E: forty eight-hour exposure X-axis: drug (ceramide derivative) concentration (micromolar); y-axis: percent cell growth. "X": N-C8 sphingosine; diamond: 1-acetate, C6-ceramide; square: 1-butyrate, C6-ceramide; triangle: 1-isobutyrate, C6-ceramide.

FIG. 10. In Vitro Sensitivity of A549 Cells to 1-Acetate, C6-Ceramide for Different Lengths of Exposure. X-axis: drug concentration (micromolar); y-axis: percent growth. Diamond: one hour; square: four hours; triangle: eight hours; X: twenty four hours; star: forty eight hours.

Figure 11:
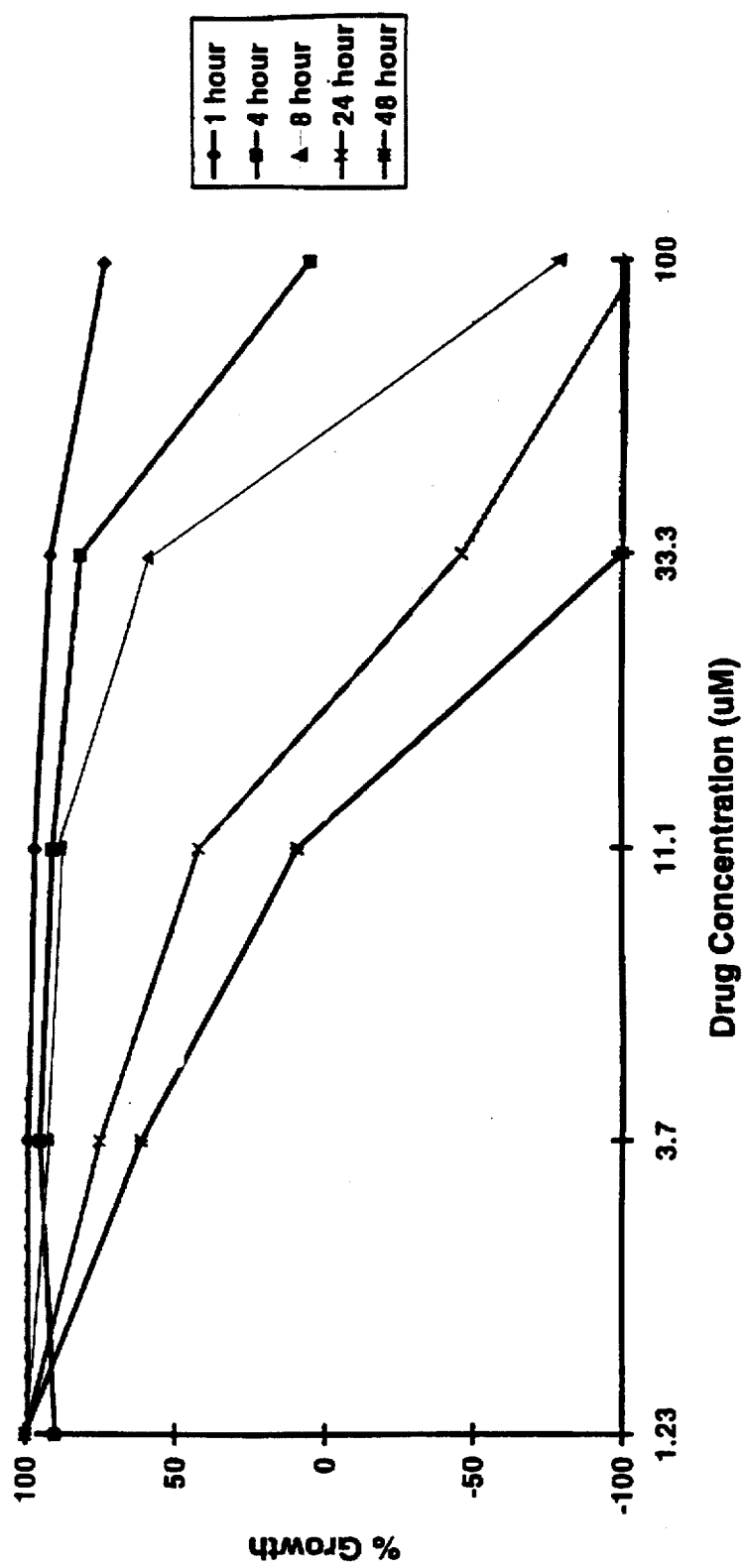

FIG. 11. In Vitro Sensitivity of A549 Cells to 1-Butyrate, C6-Ceramide for Different Lengths of Exposure. X-axis: drug concentration (micromolar); y-axis: percent growth. Diamond: one hour; square: four hours; triangle: eight hours; X: twenty four hours; star: forty eight hours.

Figure 12:
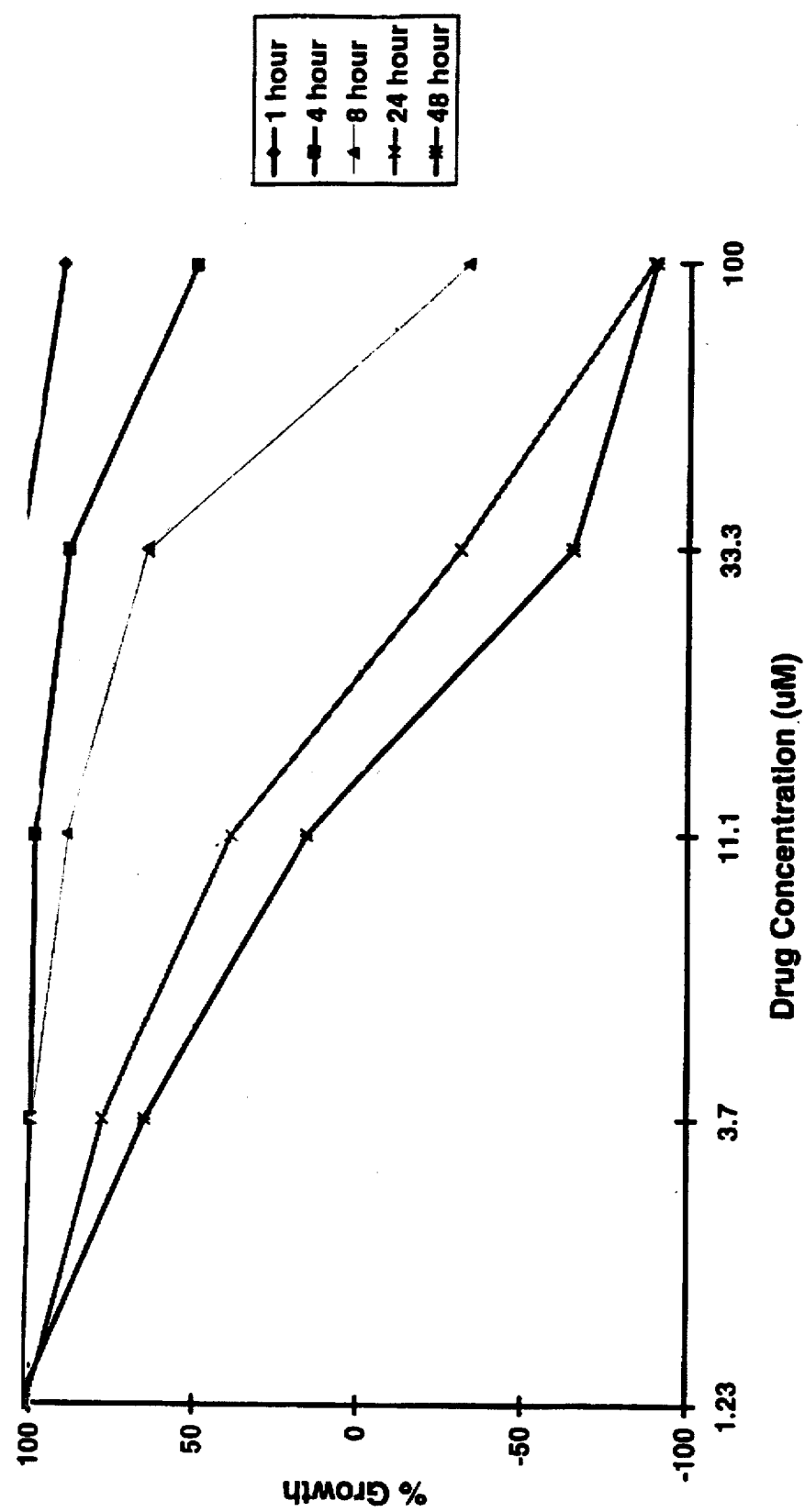

FIG. 12. In Vitro Sensitivity of A549 Cells to 1-Isobutyrate, C6-Ceramide for Different Lengths of Exposure. X-axis: drug concentration (micromolar); y-axis: percent growth. Diamond: one hour; square: four hours; triangle: eight hours; X: twenty four hours; star: forty eight hours.

Figure 13:
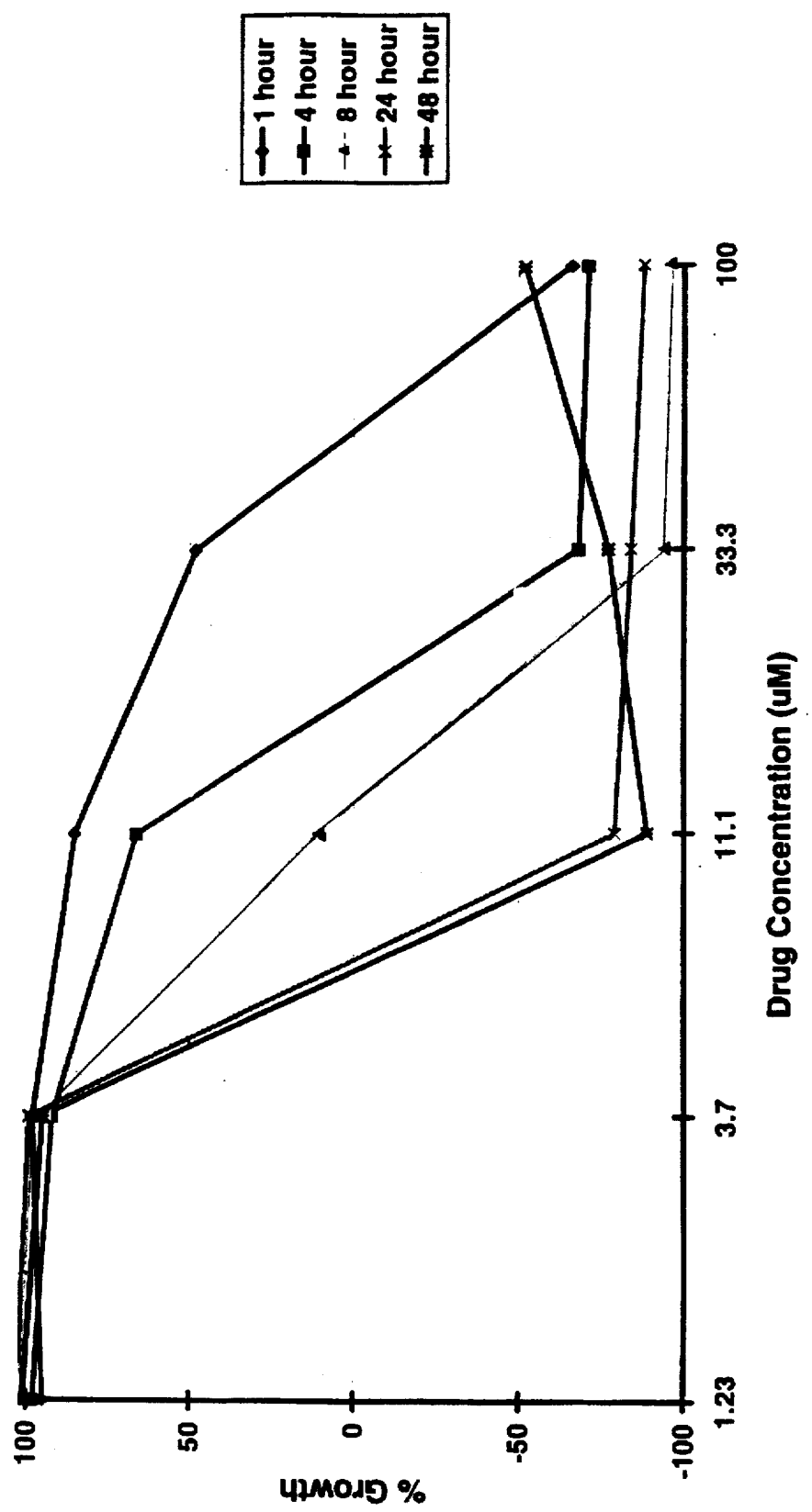

FIG. 13. In Vitro Sensitivity of A549 Cells to N-C8 Sphingosine for Different Lengths of Exposure. X-axis: drug concentration (micromolar); y-axis: percent growth. Diamond: one hour; square: four hours; triangle: eight hours; X: twenty four hours; star: forty eight hours.

Figure 14:
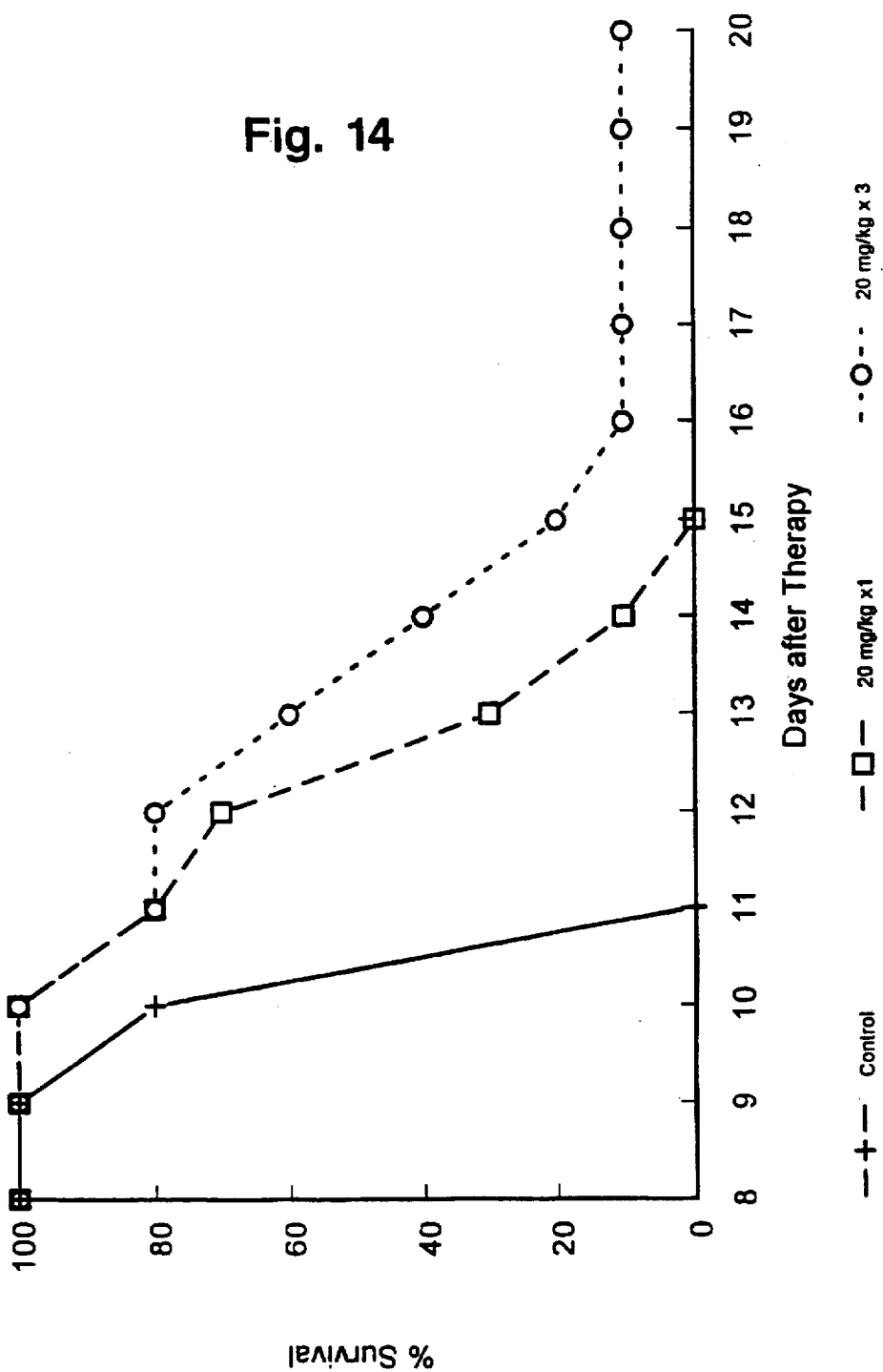

FIG. 14. Therapeutic Efficacy of N-hexyl Sphingosine Against P-388/ADR (adriamycin-resistant) Tumor-Bearing Mice. X-axis: days after therapy; y-axis: percent survival in treatment group. "+": Control (untreated); squares: one dose of 20 mg n-hexyl sphingosine per kg of body weight; circles: 3 20 mg/kg doses.

DETAILED DESCRIPTION OF THE INVENTION

Provided herein is a compound having the formula $R^1$-$Y^1$—CHZ$^1$-CH(NY$^2$Y$^3$)—CH$_2$-Z$^2$, wherein: $R^1$ is a straight-chained alkyl, alkenyl or alkynyl group having from 8 to 19 carbon atoms in the aliphatic chain; $Y^1$ is —CH═CH—, —C≡C— or —CH(OH)CH(OH)—; $Z^1$ is OH or a conversion-inhibiting group; $Z^2$ is a conversion-inhibiting group; $Y^2$ is H, a phenyl group, an alkyl-substituted phenyl group having from 1 to about 6 carbons in the alkyl chain, or an alkyl chain having from 1 to 6 carbons; $Y^3$ is H or a group having the formula —C(O)R$^2$ or —S(O)$_2$R$^2$; R$^2$ is a straight-chained alkyl, alkenyl or alkynyl group having from 1 to 23 carbon atoms in the chain; and wherein when $Z^2$ is an amino, R$^2$ is an aliphatic chain having from 1 to 9 or from 19 to 23 carbon atoms in the aliphatic chain. Preferably, $R^1$ is an alkyl group, more preferably, CH$_3$(CH$_2$)$_{12}$—, $Y^1$ is —CH═CH—, $Y^2$ is H, $Y^3$ is —C(O)R$^2$ and R$^2$ is an alkyl chain, more preferably an alkyl chain having from 6 to 8 carbons. Most preferably. R$^1$ and R$^2$ together comprise from about 15 to about 25 carbons, wherein R$^1$ preferably comprises 13 carbons and R$^2$ preferably comprises 6 to 8 carbons. Without intending to be limited by theory, it is believed that total carbon chain length of a lipid is an important factor in determining the ability of the lipid to insert itself into biological membranes.

Without intending for this invention in any way to be limited by theory, it is believed that sphingosines and ceramides can act as signal transducers or secondary messengers in cells, i.e., that intracellular levels are increased in response to external stimuli, and that this increase results in enhanced protein kinase and phosphatase activities (see, e.g., M. Raines et al., supra; R. Kolesnik et al., supra; G. Dbaibo et al., supra; and J. Fishbein et al., supra). Activated protein kinases and phosphatases can activate cellular processes which lead to cell death. Accordingly, it can be therapeutically desirable to increase intracellular concentrations of sphingosines and ceramides in cancer cells.

Figure 1:
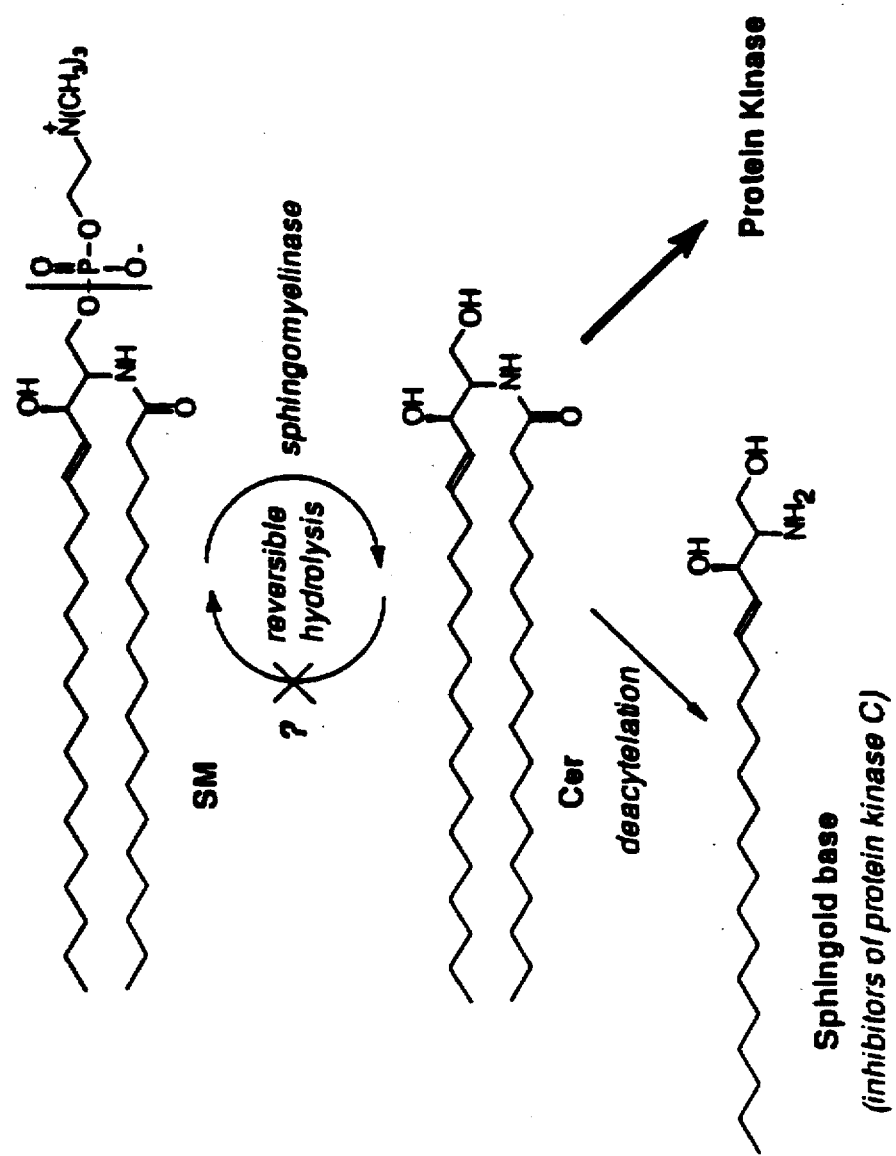
FIG. 1. Ceramide Metabolism. Cer: ceramides; SM.
Figure 2B:
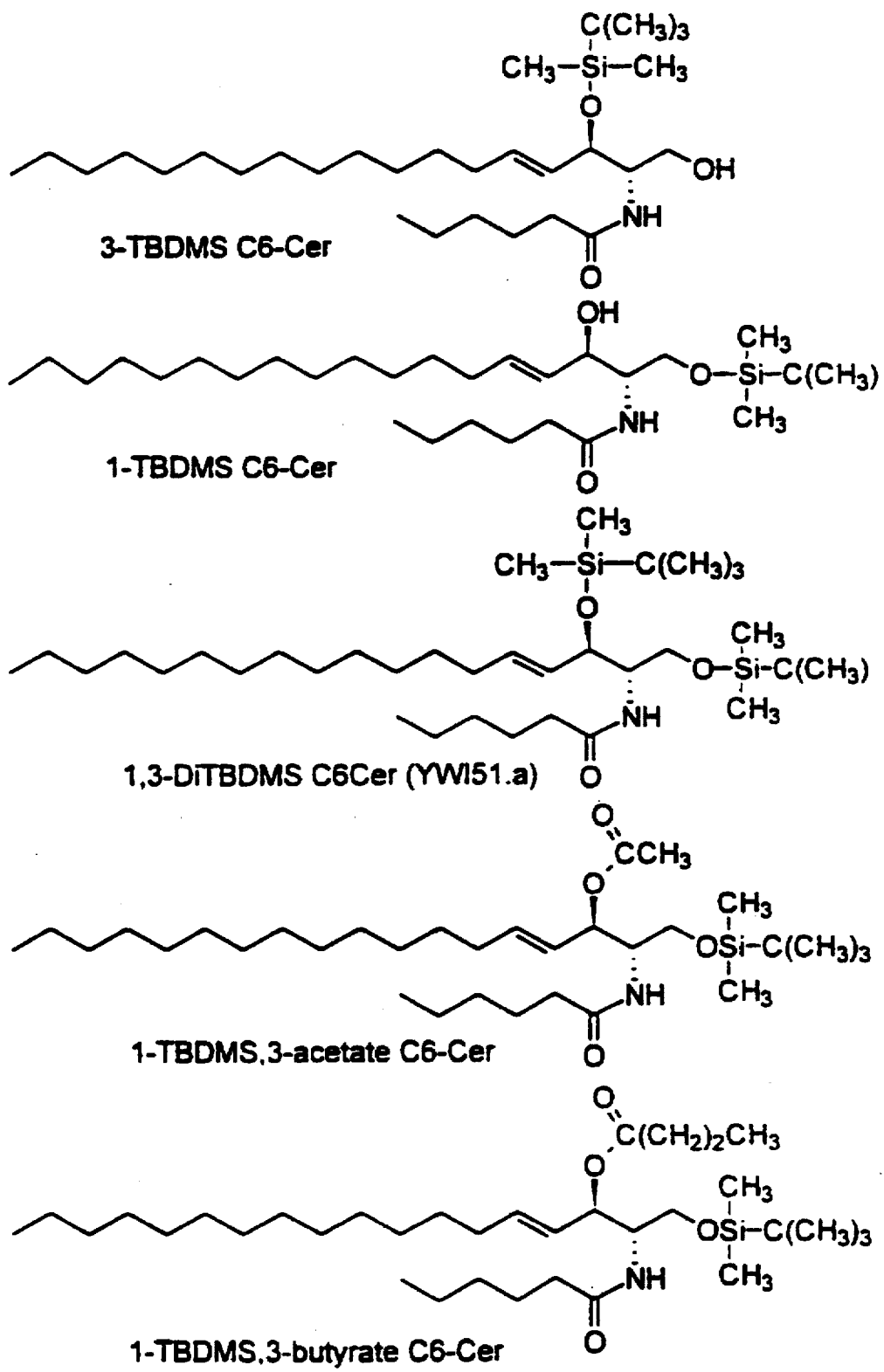
Figure 2C:
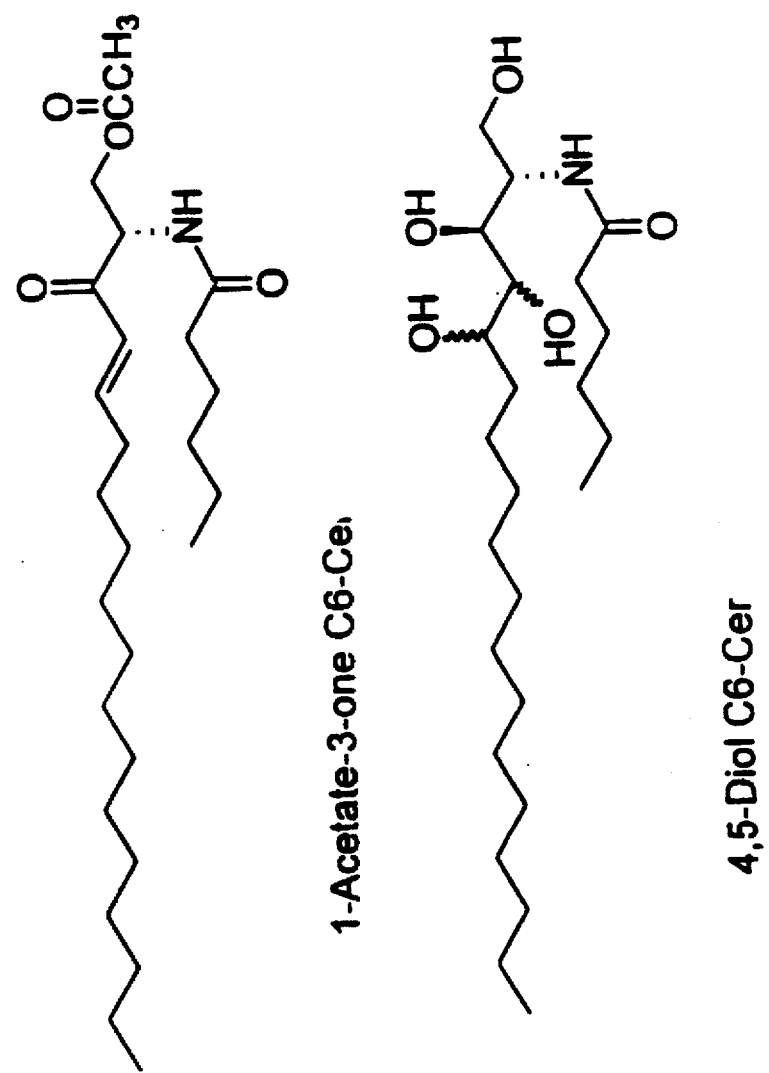
Figure 2D:
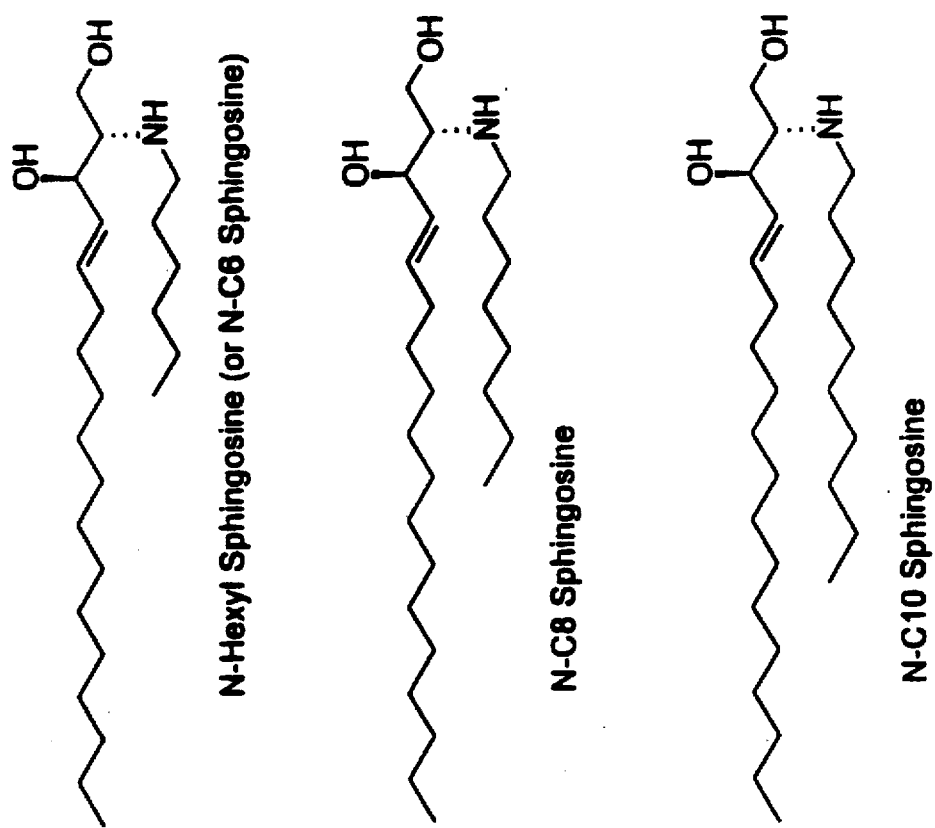

Sphingosines and ceramides are formed in animal cells by the combination of palmitoyl CoA (CH$_3$(CH$_2$)$_{14}$—CO—S—CoA) and serine to give dehydrosphinganine (CH$_3$(CH$_2$)$_{14}$Co—CH(NH$_3$)—CH$_2$OH and CO$_2$ (see, e.g., L. Stryer, Biochemistry (2nd edition), W. H. Freeman and Co., New York, pp. 461–462)). Dehydrosphinganine is converted to dihydrosphingosine (CH$_3$(CH$_2$)$_{14}$—CH(OH)—CH(NH$_3$)—CH$_2$OH) which is then converted to sphingosine (CH$_3$(CH$_2$)$_{12}$CH═CH—CH(OH)—CH(NH$_3$)—CH$_2$OH). A fatty acid is then linked to the amide group of sphingosine to give rise to a ceramide (CH$_3$(CH$_2$)$_{12}$CH═CH—CHOH—CH(CH$_2$OH)—NH—CO—R, where R is a fatty acid chain). A phosphorylcholine group (PO$_4$CH$_2$CH$_2$—N(CH$_3$)$_3$) can be attached to the ceramide at its hydroxyl group to produce a sphingomyelin (CH$_3$(CH$_2$)$_{12}$CH═CH—CHOH—CH (CH$_2$PO$_4$CH$_2$CH$_2$—N(CH$_3$)$_3$)—NH—CO—R). Sphingomyelinase can catalyze the hydrolytic removal of the phosphorylcholine from the sphingomyelin to give rise to a ceramide (see, e.g., FIG. 1). Reverse hydrolysis of the ceramide can give rise to a sphingomyelin.

Blockage or inhibition of this "reverse hydrolysis" step, that is, conversion of a ceramide to the corresponding sphingomylein, can lead to increased intracellular ceramide levels. "Conversion-inhibiting groups" are attached to sphingosines and ceramides to inhibit sphingomylein formation therefrom. Such groups are generally not found attached to sphingosines and ceramides, or their biosynthetic precursors, in animal cells The compounds of this invention are synthesized by a number of routes well known to and readily practiced by ordinarily skilled artisans, given the teachings of this invention (see, for example, below, wherein "rf" refers to one of the following references: 1: J. Am. Chem. Soc., 94: 6190 (1972); 2: J. Org. Chem. 59: 668 (1994); 3: Angew. Chem., Intl. Ed. (English), 17: 569 (1978); 4: *Vogel's Textbook of Practical Organic Chemistry* (5th ed.), pp. 769–780); 5: J. Org. Chem. 40: 574 (2975); 6: J. Org. Chem, 59: 182 (1994); 7: J. Org. Chem. 25: 2098 (1960); 8: Synthesis (1985): pp. 253–268; 9: J. Chem. Soc. (1953): p. 2548; 10: J. Am. Chem. Soc. 90: 4462, 4464 (1968); 11: *Oxidations in Organic Chemistry* (Am. Chem. Soc, Washington, D.C. (1990), pp. 60–64; 12: J. Med. Chem. 30 1326 (1987); 13: Synth. Commun. 9: 757 (1979); 14: *The Chemistry of Amides* (J. Wiley & Sons, New York (2970)), pp. 795–801; 15: J. Med. Chem. 37: 2896 (1994); 4: J. Med. Chem. 30: 1326 (1987); 16: Rec. Chem. Prog. 29: 85 (1968); and 17: *Phosoholipids Handbook* (Marcell Dekker, Inc., New York (1993), p. 97); the contents of these are incorporated herein by reference).

For example, such artisans would use a sphingosine or a ceramide as their starting material. Alkyl, alkenyl or alkynyl chains of varying length can be attached thereto, or removed therefrom, by known means. Conversion-inhibiting groups can also be attached to the sphingosines and ceramides by known means. These include, without limitation, oxidation/reduction, substitution, condensation and alkylation reactions, as well as other generally accepted means for attaching and removing chemical groups from a compounds and for converting compounds from one form to another. Such reactions are generally formed using generally accepted solvents and are performed under readily determinable conditions.

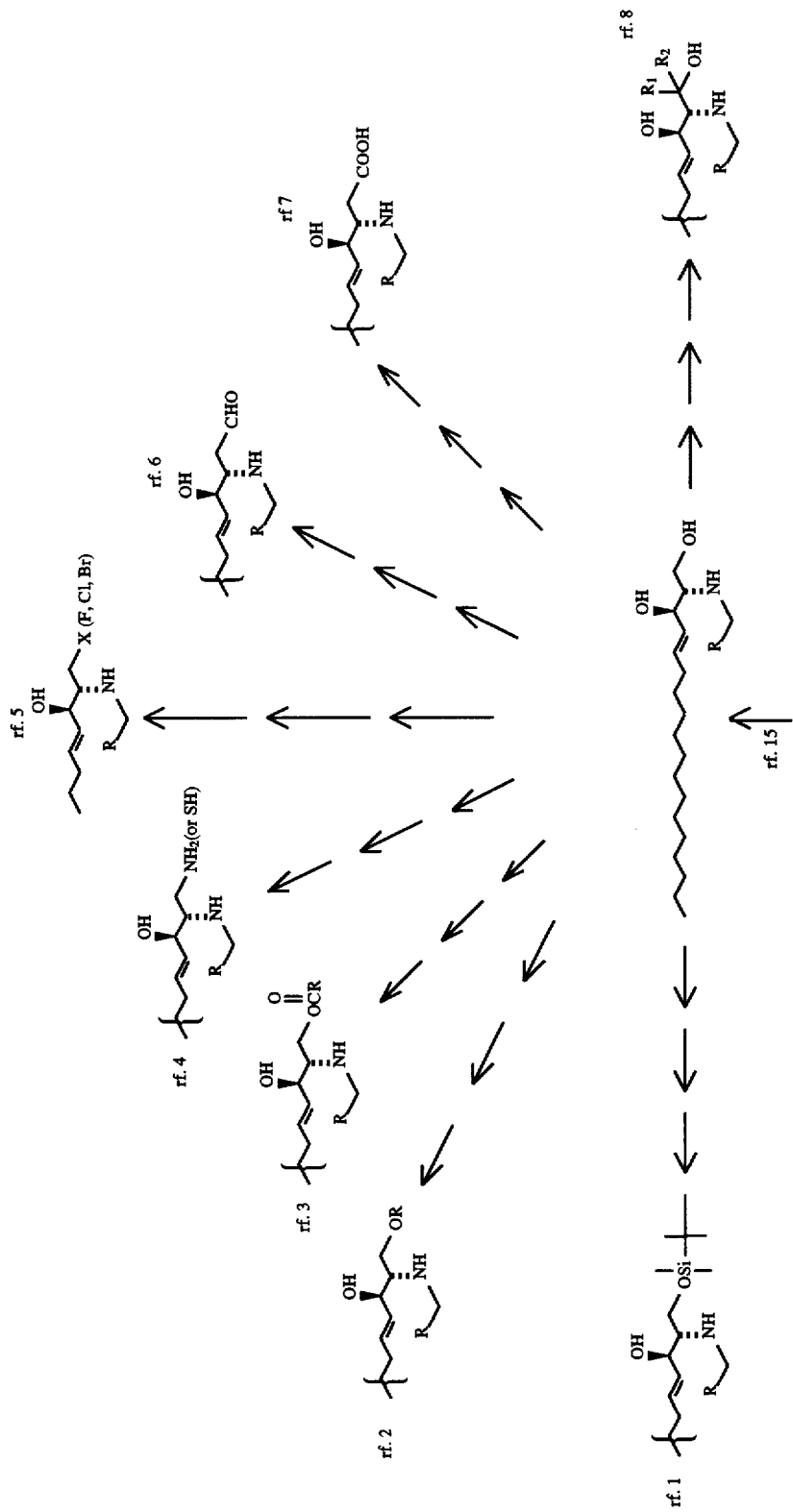

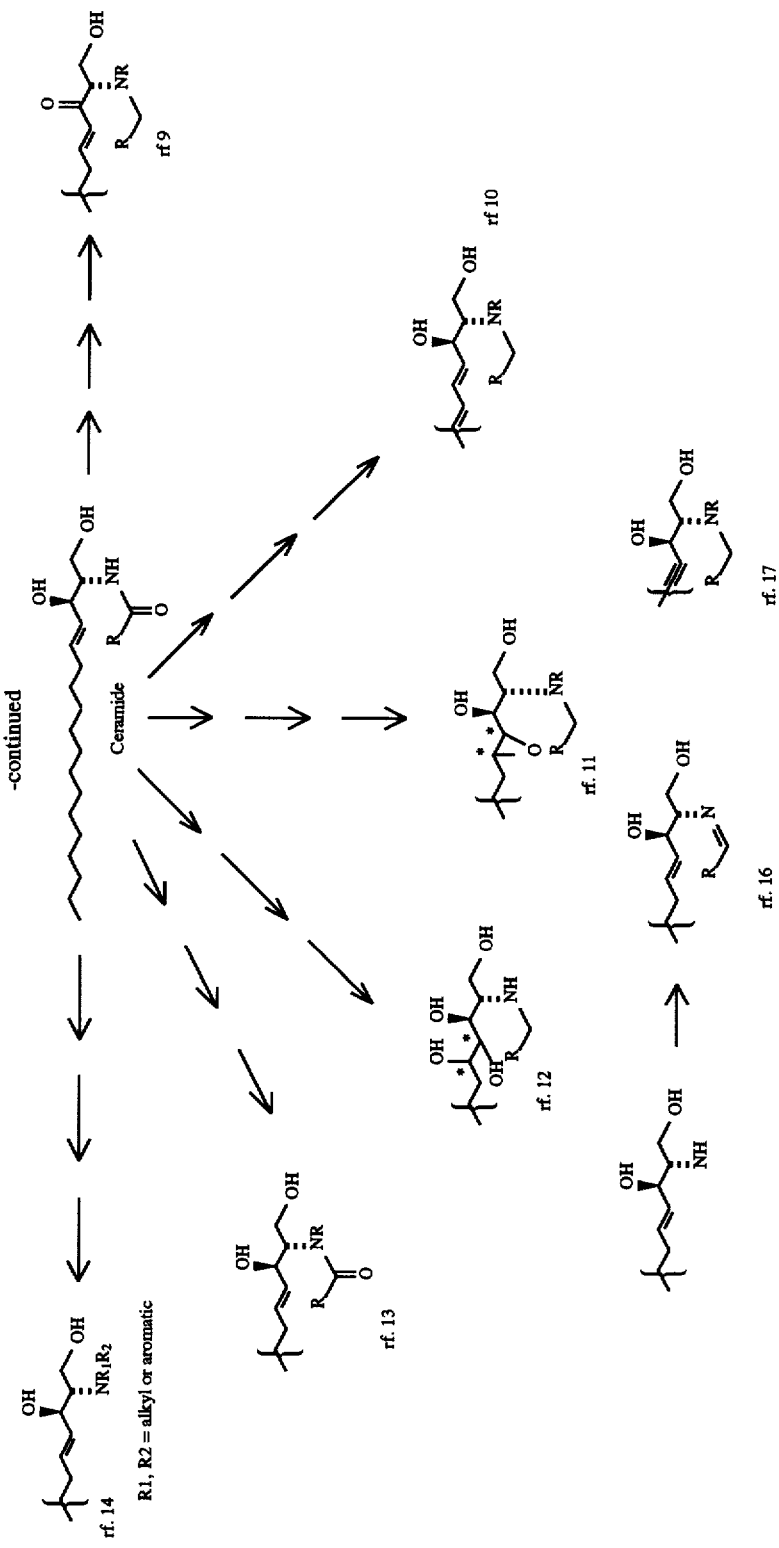

Specific compounds can be synthesized as follows. Synthesis of sily ether of ceramide: a mixture of ceramide and t-butyldimethylsilyl chloride (1 equivalent) and imidazole (2 equivalent) in DMF is stirred under $N_2$ at room temperature overnight. The solvent is then removed under a stream of $N_2$ and residue is dissolved in $CH_2Cl_2$, washed ($H_2O$), dried ($MgSO_4$) and concentrated to dryness. The residue is purified over silica gel (AcOEt: Hexan=1:3). Synthesis of 1-ester ceramide: The mixture of ceramide and Ac2O (1 equivalent) and catalytic amount of dimethyl amino pyridine in dry CH2Cl2 is stirred at room temperature for 1 hour and the reaction is checked by TLC (AcOEt). The mixture is then concentrated. The crude product is purified over silica gel (AcOEt: Hexane=2:3.5) Oxidation of C3-OH of ceramide to ketone: 1-OAc ceramide is dissolved in acetone and cooled in an ice-bath. Jone's reagent is dropwised slowly till the orange color persists. The reaction is quenched by isopropanol, and $NaHCO_3$ is added and stirred for 5 minutes. The solution is filtered and concentrated to dryness. The crude product was purified by preparative TLC (ACOET: Hexane= 1:2.5). Reduction of ceramide to sphingosine analogs: To an ice-cold stiffed solution of ceramide in anhydrous THF is added $LiAlH_4$ and the mixture is stirred at room temperature under $N_2$ for 24 hours. Under ice cooling, the reaction mixture is quenched by addition of saturated aqueous $NaHCO_3$. The resulting slurry is filtered and washed with THF. The solution is concentrated and the residue is brought into $CH_2Cl_2$, washed with $H_2O$, dried ($MgSO_4$) and concentrated to dryness. The residue is then purified over preparative TLC (silica gel) $CH_2Cl_2$:MeOH:TEA=8:1:0.08. Synthesis of 4,5-diol ceramide: To a solution of ceramide in a mixture of $Me_2CO$ distilled $H_2O$ and t-BuOH, N-Methyl morpholine N-oxide (NMO, 1.2 equivalent) and $OsO_4$ (catalytic amount) in THF are added. The reaction mixture is stirred at 45° C. for 6 hours, quenched by solid $NaHCO_3$, and the mixture is then stirred for 15 minutes. The suspension is filtered, and the filtrate dissolved in THF; the solution is then washed with brine. The organic solution is separated, dried and concentrated to dryness. The residue is purified over preparative TLC (THF).

Suitable conversion-inhibiting groups can be identified by a number of meanns readily practiced by ordinarily skilled artisans, given the motivation by this invention to identify such groups. For example, and without limitation, such artisans can select a chemical moiety, and attach it to a sphingosine or ceramide as described above. The artisans can then readily determine the relative rate at which such a compound undergoes hydrolysis, and the rate at which a sphingmyelin is formed from the compound. Rates of hydrolysis are themselves readily determinable by ordinarily skilled artisans, for example and without limitation, by attaching a radioactive moiety to a sphingosine or ceramide and then following the rate of hydrolytic cleavage of the moiety by chromatographic means. Rates of sphingomyelin formation are also readily determinable, for example and without limitation, by combining radioactive phosphorylcholine with a conversion-inhibiting group-containing compound in an enzyme system capable of attaching the phosphorylcholine to the compound, and then using chromatographic means to assess the rate at which the phosphorylcholine is added. Preferred conversion-inhibiting groups are those which most inhibit hydrolysis and phosphorylcholine attachment.

Conversion-inhibiting groups can have the formula $-X^2X^3$ or $-O-X^2X^3$, wherein $X^2$ is selected from the group consisting of $CH_2-$, $C(CH_3)_2-$, $Si(PO_4)_2-$, $Si(CH_3)_2-$, $SiCH_3PO_4-$, $C(O)-$ and $S(O)_2-$ and wherein $X^3$ is selected from the group consisting of $-C(O)H$, $-CO_2H$, $-CH_3$, $-C(CH_3)_3$, $-Si(CH_3)_3$, $-SiCH_3(C(CH_3)_3)_2$, $-Si(C(CH_3)_3)_3$, $-Si(PO_4)_2C(CH_3)_3$, a phenyl group, an alkyl-substituted phenyl group having from 1 to 6 carbons in the alkyl chain, an alkyl chain having from 1 to 6 carbons, an amino moiety, a fluorine, a chlorine, or a group having the formula $C(R^3R^4)OH$; each of $R^3$ and $R^4$ is independently an alkyl chain having from 1 to 6 carbons, a phenyl group or an alkyl-substituted phenyl group having from 1 to 6 carbons in the alkyl chain. Preferably, the conversion-inhibiting group is $-OC(O)CH_3$, $-OC(O)CH_2CH_2CH_3$, $-OC(O)CH(CH_3)CH_3$, or $-OSi(CH_3)_2C(CH_3)_3$ (TBDMS) more preferably, $-OSi(CH_3)_2C(CH_3)_3$.

Conversion-inhibiting groups can also have the formula $-X^1$ or $-OX^1$, wherein $X^1$ is $C(O)H$, $CO_2H$, $CH_3$, $C(CH_3)_3$, $Si(CH_3)_3$, $SiCH_3(C(CH_3)_3)_2$, $Si(C(CH_3)_3)_3$, $Si(PO_4)_2C(CH_3)_3$, a phenyl group, an alkyl-substituted phenyl group having from 1 to 6 carbons in the alkyl chain, an alkyl chain having from 1 to 6 carbons, an amino moiety, a flourine, a chlorine, or a group having the formula $C(R^3R^4)OH$; each of $R^3$ and $R^4$ is independently an alkyl chain having from 1 to 6 carbons. Conversion-inhibiting groups include attachment of chemical moieties to sphingosines and ceramides by ether, silyl ether, ester, acetal and sulfonate linkages.

Preferably, the compound of this invention has the formula $CH_3(CH_2)_{12}-CH=CH-CH_2Z^1-CH(NHY^3)-CH_2-Z^2$. $Y^3$ is then preferably a group having the formula $-C(O)R^2$, more preferably, $-C(O)(CH_2)_4CH_3$. $Z^2$ is preferably $-OSi(CH_3)_2C(CH_3)_3$, $-OSi(PO_4)_2C(CH_3)_3$, $-C(O)CH_3$ or $-OC(O)CH_2CH_2CH_3$.

Also provided herein is a pharmaceutical composition comprising the compound of this invention and a pharmaceutically acceptable carrier; the composition can also comprise an additional bioactive agent. "Pharmaceutically acceptable carriers" as used herein are generally intended for use in connection with the administration of lipids and liposomes, including liposomal bioactive agent formulations, to animals, including humans. Pharmaceutically acceptable carriers are generally formulated according to a number of factors well within the purview of the ordinarily skilled artisan to determine and account for, including without limitation: the particular liposomal bioactive agent used, its concentration, stability and intended bioavailability; the disease, disorder or condition being treated with the liposomal composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985)). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and antioxidants.

Further provided is a method of administering a bioactive compound to an animal, preferably a human, which comprises administering to the animal this composition; the method can comprise administering an additional bioactive agent to the animal. The administration, which can be by any means generally accepted for administering pharmaceutical products to animals, is generally intravenous administration.

The animal can be afflicted with a cancer, wherein the method comprises administering an amount of the composition which comprises an anticancer effective amount of the compound. Treatable cancers include, without limitation, brain, breast, lung, ovarian, colon, stomach or prostate cancers, and can be sarcomas, carcinomas, neuroblastomas, or gliomas, amongst others. Drug resistant cancers can also be treated.

"Anticancer effective amounts" of the compound of this invention are generally amounts effective to inhibit, ameliorate, lessen or prevent establishment, growth, metastasis or invasion of one or more cancers in animals to which the compound has been administered. Anticancer effective amounts are generally chosen in accordance with a number of factors, e.g., the age, size and general condition of the subject, the cancer being treated and the intended route of administration, and determined by a variety of means, for example, dose ranging trials, well known to, and readily practiced by, ordinarily skilled artisans given the teachings of this invention. Typically, the anticancer effective amount of the compound is at least about 0.1 mg of the compound per kg of body weight of the animal. Generally, the anticancer effective amount is from about 1 mg per kg to about 50 mg per kg.

Provided herein is a liposome having a bilayer which comprises a lipid and a compound having the formula $R^1-Y^1—CHZ^1-CH(NY^2Y^3)—CH_2-Z^2$, wherein: $R^1$ is a straight-chained alkyl, alkenyl or alkynyl group having from 5 to 19 carbon atoms in the chain; $Y^1$ is —CH=CH—, —C≡C— or —CH(OH)CH(OH)—; each of $Z^1$ and $Z^2$ is independently OH or a conversion-inhibiting group; $Y^2$ is H, a phenyl group, an alkyl-substituted phenyl group having from 1 to 6 carbons in the alkyl chain, or an alkyl chain having from 1 to 6 carbons; $Y^3$ is H or a group having the formula -$R^2$, —$C(O)R^2$ or —$S(O)_2R^2$; $R^2$ is a straight-chained alkyl, alkenyl or alkynyl group having from 1 to 23 carbon atoms; and wherein the bilayer comprises at least about five mole percent of the compound.

Liposomes are self-assembling structures comprising one or more lipid bilayers, each of which surrounds an aqueous compartment and comprises two opposing monolayers of amphipathic lipid molecules. These comprise a polar (hydrophilic) headgroup region covalently linked to one or two non-polar (hydrophobic) acyl chains. Energetically unfavorable contacts between the hydrophobic acyl chains and the aqueous medium are generally believed to induce lipid molecules to rearrange such that the polar headgroups are oriented towards the aqueous medium while the acyl chains reorient towards the interior of the bilayer. An energetically stable structure is formed in which the acyl chains are effectively shielded from coming into contact with the aqueous medium.

Liposomes can be made by a variety of methods (for a review, see, for example, Deamer and Uster (1983)). These methods include without limitation: Bangham's methods for making multilamellar liposomes (MLVs); Lenk's, Fountain's and Cullis' methods for making MLVs with substantially equal interlamellar solute distribution (see, for example, U.S. Pat. Nos. 4,522,803, 4,588,578, 5,030,453, 5,169,637 and 4,975,282); and Paphadjopoulos et al.'s reverse-phase evaporation method (U.S. Pat. No. 4,235,871) for preparing oligolamellar liposomes. Unilamellar vesicles can be produced from MLVs by such methods as sonication (see Paphadjopoulos et al. (1968)) or extrusion (U.S. Pat. No. 5,008,050 and U.S. Pat. No. 5,059,421). The ether lipid liposome of this invention can be produced by the methods of any of these disclosures, the contents of which are incorporated herein by reference.

Various methodologies, such as sonication, homogenization, French Press application, milling and extrusion can be used to size reduce liposomes, that is to prepare liposomes of a smaller size from larger liposomes. Tangential flow filtration (see WO89/008846), can also be used to regularize the size of liposomes, that is, to produce liposomes having a population of liposomes having less size heterogeneity, and a more homogeneous, defined size distribution. The liposome of this invention can be unilamellar or multilamellar.

Liposomal bilayers can comprise a variety of ampipathic lipids, including those which are saturated or unsaturated, and which typically have acyl chains of from 10 to 24 carbons. Suitable polar groups include, without limitation, phosphorylcholine, phosphorylethanolamine, phosphorylserine, phosphorylglycerol and phosphorylinositiol. Suitable acyl chains include, without limitation, laurate, myristate, palmitate, stearate and oleate chains. Liposomal bilayers can further comprise sterols, such as cholesterol. Sterols generally affect the fluidity of lipid bilayers, typically increasing the fluidity of bilayer hydrocarbon chains below the gel-to-liquid transition temperature (Tm), and decreasing fluidity above the Tm (see, for example, Lewis and McElhaney (1992) and Darnell et al. (1986)) Accordingly, sterol interactions with surrounding hydrocarbon chains generally inhibit emigration of these chains from the bilayer.

Preferably, the liposomal bilayer comprises at least about 10 mole percent of the compound. When $Y^3$ is $R^2$, it is then preferably, —$(CH_2)_3CH_3$, —$(CH_2)_5CH_3$, —$(CH_2)_7CH_3$, or —$(CH_2)_9CH_3$, and more preferably, $(CH_2)_5CH_3$. When $Y^3$ is —$C(O)R^2$, it is then preferably —$C(O)(CH_2)_4CH_3$. Preferably, the liposome comprises a compound having the formula $CH_3—(CH_2)_{12}—CH=CH—CH_2Z^1-CH(NHY^3)—CH_2Z^2$; more preferably, the compound comprises at least one conversion-inhibiting group, such as —$OC(O)CH_3$, —$OC(O)CH_2CH_3$, —$OC(O)CH(CH_3)CH_3$, or —$OSi(CH_3)_2C(CH_3)_3$. More preferably, the conversion-inhibiting group is $OSi(CH_3)_2C(CH_3)_3$ (TBDMS).

Intracellular ceramide levels can also be increased by administration of vitamin D3, either separately from administration of the compounds and liposomes of this invention, or more preferably, in connection with the administration of liposomes. Without intending in any way to be limited by theory, it is believed that vitamin D3 can stimulate sphingomyelinase to convert sphingomyelins to ceramides. Preferably, bilayers containing vitamin D3 contain about 1 mole percent of vitamin $D_3$.

The liposome can comprise an additional bioactive agent. A "bioactive agent," is any compound or composition of matter that can be administered to animals, preferably humans. Such agents can have biological activity in animals; the agents can also be used diagnostically in the animals. Bioactive agents include therapeutic and imaging agents. Bioactive agents which may be associated with liposomes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as tolic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labelled compounds; radiopaque compounds; fluorescent compounds; mydriatic compounds; bronchodilators; local anesthetics; and the like. Liposomal bioactive agent formulations can enhance the therapeutic index of the bioactive agent, for example by buffering the agent's toxicity. Liposomes can also reduce the rate at which a bioactive agent is cleared from the circulation of animals. Accordingly, liposomal formulation of bioactive agents can mean that less of the agent need be administered to achieve the desired effect. Additional bioactive agents preferred for the liposome of this invention include antimicrobial, anti-inflammatory and antineoplastic agents, or therapeutic lipids, for example, ceramides. Most preferably, the additional bioactive agent is an antineoplastic agent.

Liposomes can be loaded with one or more biologically active agents by solubilizing the agent in the lipid or aqueous phase used to prepare the liposomes. Alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056 and WO86/01102).

The liposome of this invention can comprise a headgroup-modified lipid. "Headgroup-modified lipids" are lipids which, when incorporated into the lipid bilayers of liposomes can inhibit clearance of the liposomes from the circulatory systems of animals to which they have been administered. Liposomes are cleared from an animal's body by way of its reticuloendothelial system (RES) which consists of fixed and circulating macrophages. Avoiding RES clearance can allow liposomes to remain in the circulation longer, meaning that less of the drug need be administered to achieve desired serum levels. Enhanced circulation times can also allow targeting of liposomes to non-RES containing tissues. Liposomal surfaces can become coated with serum proteins when administered to animals, i.e., liposomes can be opsonized. Rates of clearance by the RES can be related to the rate and level of opsonization; accordingly, clearance can be inhibited by modifying the outer surface of liposomes such that binding of serum proteins is generally inhibited. This can be accomplished by minimizing or shielding negative surface charges, which can promote protein binding, or by otherwise presenting a steric hindrance to the binding of serum proteins.

Effective surface modification, that is, alterations to the outer surfaces of liposomes which result in inhibition of opsonization and RES uptake, can be accomplished by incorporating headgroup-modified lipids into liposomal bilayers. "Headgroup-modified lipids" as used herein are amphipathic lipids whose polar headgroups have been derivatized by attachment thereto of a chemical moiety, e.g., polyethylene glycol, a polyalkyl ether, a ganglioside, an organic dicarboxylic acid or the like, which can inhibit the binding of serum proteins to liposomes such that the pharmacokinetic behavior of the vesicles in the circulatory systems of animals is altered (see, e.g., Blume et al., Biochim. Biophys. Acta. 1149:180 (1993); Gabizon et al., Pharm. Res. 10(5):703 (1993); Park et al. Biochim. Biophys Acta. 1108:257 (1992); Woodle et al., U.S. Pat. No. 5,013, 556; Allen et al., U.S. Pat. Nos. 4,837,028 and 4,920,016; U.S. Ser. No. 142,691, filed Oct. 25, 1993; the contents of these disclosures are incorporated herein by reference).

The amount of a headgroup-modified lipid incorporated into the liposome depends upon a number of factors well known to the ordinarily skilled artisan, or within his purview to determine without undue experimentation. These include, but are not limited to: the type of lipid and the type of headgroup modification; the type and size of the liposome; and the intended therapeutic use of the liposomal formulation. Typically, the concentration of the headgroup-modified lipid in the lipid bilayer of the liposome is at least about five mole percent, desirably, about ten mole percent.

The liposome of this invention can be dehydrated, stored and then reconstituted such that a substantial portion of their internal contents are retained in the liposomes. Liposomal dehydration generally requires use of a hydrophilic drying protectant (see U.S. Pat. Nos. 4,229,360 and 4,880,635). This hydrophilic compound is generally believed to prevent the rearrangement of the lipids in the liposome, so that the size and contents are maintained during the drying procedure and through rehydration, such that the liposomes can be reconstituted. Appropriate qualities for such drying protectants are that they be strong hydrogen bond acceptors, and possess stereochemical features that preserve the intramolecular spacing of the liposome bilayer components. Saccharide sugars, preferentially mono- and disaccharides, are suitable drying protectants for liposomes. Alternatively, the drying protectant can be omitted if the liposome preparation is not frozen prior to dehydration, and sufficient water remains in the preparation subsequent to dehydration.

Also provided herein is a pharmaceutical composition comprising the liposome of this invention and a pharmaceutically acceptable carrier. Further provided is a method of administering a compound to an animal which comprises administering to the animal this composition. The method can be used to treat an animal afflicted with a cancer, wherein a dose of the composition is administered and wherein the dose comprises an anticancer effective amount of the liposome. Typically, the dose comprises at least about 1 mg of the liposome per kg of body weight of the animal. Generally, the dose comprises from about 1 mg per kg to about 1000 mg per kg.

Provided herein is a liposome having a bilayer which comprises a lipid and a compound having the formula $R^1-Y^1-CHZ^1-CH(NY^2Y^3)-CH_2-Z^2$, wherein: $R^1$ is a straight-chained alkyl, alkenyl or alkynyl group having from 5 to 19 carbon atoms in the chain; $Y^1$ is $-CH=CH-$, $-C\equiv C-$ or $-CH(OH)CH(OH)-$; each of $Z^1$ and $Z^2$ is independently OH or a conversion-inhibiting group; $Y^2$ is H, a phenyl group, an alkyl-substituted phenyl group having from 1 to 6 carbons or an alkyl chain having from 1 to 6 carbons; $Y^3$ is H or a group having the formula $-R^2$, $-C(O)R^2$ or $-S(O)_2R^2$; $R^2$ is a straight-chained alkyl, alkenyl or alkynyl group having from 1 to 23 carbon atoms; and wherein the bilayer comprises an anticancer-effective amount of the compound. Also provided is a pharmaceutical composition comprising this liposome and a pharmaceutically acceptable carrier. Further provided is a method of treating an animal afflicted with a cancer which comprises administering to the animal this composition.

EXAMPLES

Example 1

Liposome Preparation

Liposomes were prepared with the components, and at the mole ratios of components, indicated in Table 1 (see below) by the solvent evaporation method. For example, PC/Chol/ C2-ceramide liposomes were prepared by dissolving 1.8242 mg bovine phosphatidylcholine (BPC), 0.4639 mg cholesterol (Chol) and 0.1366 mg C2-ceramide (C2) in a chloroform/methanol solvent mixture (2:1, volume/ volume). The solvent was then evaporated to produce dried lipid, and the dried lipid was rehydrated with HEPES buffered saline (10 mM HEPES, 150 mM NaCl, pH 7.4). For vitamin D3-containing preparations, 0.0154 mg vitamin D3 was added to the lipid mixture. For C6-ceramide-containing preparations, 0.1590 mg C6 ceramide (C6) was substituted for the C2 ceramide. For sphingomyelin (SM)-containing preparations, 2.0470 mg SM, 0.4639 mg cholesterol and 0.0154 mg vitamin D3 were used. Furthermore, the PC/Chol and PC/Chol/D3 preparations were prepared with 2.1280 mg BPC, 0.4639 mg cholesterol and 0.0154 mg vitamin D3.

TABLE 1

LIPOSOME PREPARATION

| COMPONENTS | MOLAR RATIO |
|---|---|
| PC:Chol:C2 | 6:3:1 |
| PC:Chol:C2:D3 | 6:3:1:0.1 |
| PC:Chol:C6 | 6:3:1 |
| PC:Chol:C6:D3 | 6:3:1:0.1 |
| SM:Chol | 7:3 |
| SM:Chol:D3 | 7:3:0.1 |
| PC:Chol | 7:3 |
| PC:Chol:D3 | 7:3:1:0.1 |

PC: phosphatidylcholine; Chol: cholesterol; C2: C2 ceramide: D3: vitamin D3; C6: C6 ceramide; SM: sphingomyelin.

Example 2

Figure 3:
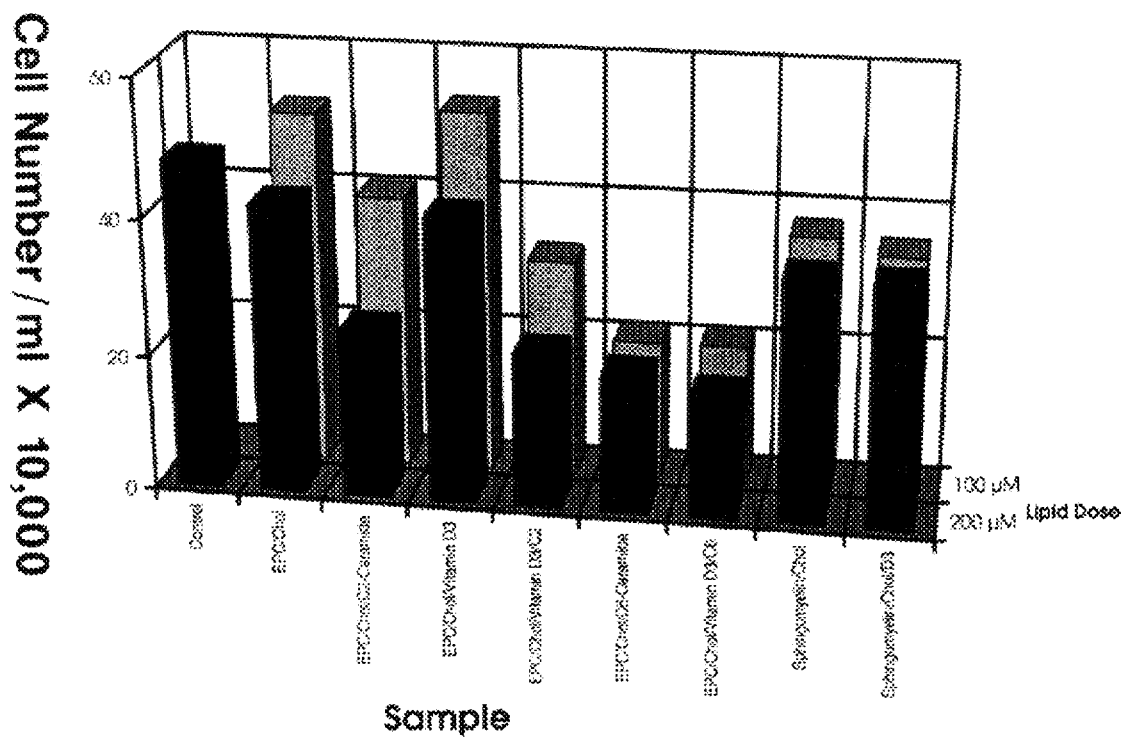
FIG. 3. Effect of Various Liposomal Ceramide/Sphingomyelin Formulations on the Growth of HL-60 Cells. The number of viable cells (per ml×10,000, y-axis) was determined for lipid doses of 100 μM and 200 μM (z-axis). X-axis: control, egg phosphatidylcholine/cholesterol (EPC/Chol), EPC/Chol/C2-ceramide (C2), EPC/Chol/vitamin D3 (D3), EPC/Chol/D3/C2, EPC/Chol/C6-ceramide (C6), EPC/Chol/D3/C6, SM/Chol and SM/Chol/D3 liposomes.

Effect of Various Liposomal Ceramide/ Sphingomyelin Formulations on the Growth of HL-60 Cells $2 \times 10^5$ HL-60 cells were incubated with egg phosphatidylcholine/cholesterol (EPC/Chol), EPC/Chol/C2-ceramide (C2), EPC/Chol/Vitamin D3 (D3), EPC/Chol/D3/C2, EPC/Chol/C6-ceramide (C6), EPC/Chol/D3/C6, sphingomyelin (SM)/Chol and SM/Chol/D3 liposomes, as well as with buffer (no liposomes; "control") and with egg phosphatidylcholine/cholesterol (EPC/Chol) liposomes. Incubation was at 37 degrees C. in serum-free medium, supplemented with 5 mg/L insulin and 5 mg/L transferrin, for 24 hours. Fetal calf serum was then added to the culture medium to a final concentration of 10%; the cells were then incubated for another 24 hours, after which the number of viable cells in each culture were counted using trypan blue staining and a hemocytometer. The number of viable cells was determined for lipid doses of 100 µM and 200 µM, and is given in the figures (below) as the number of viable cells per ml of culture medium, times 10,000. Results are reported in FIG. 3 and Table 2 (see below).

Example 3

Figure 4:
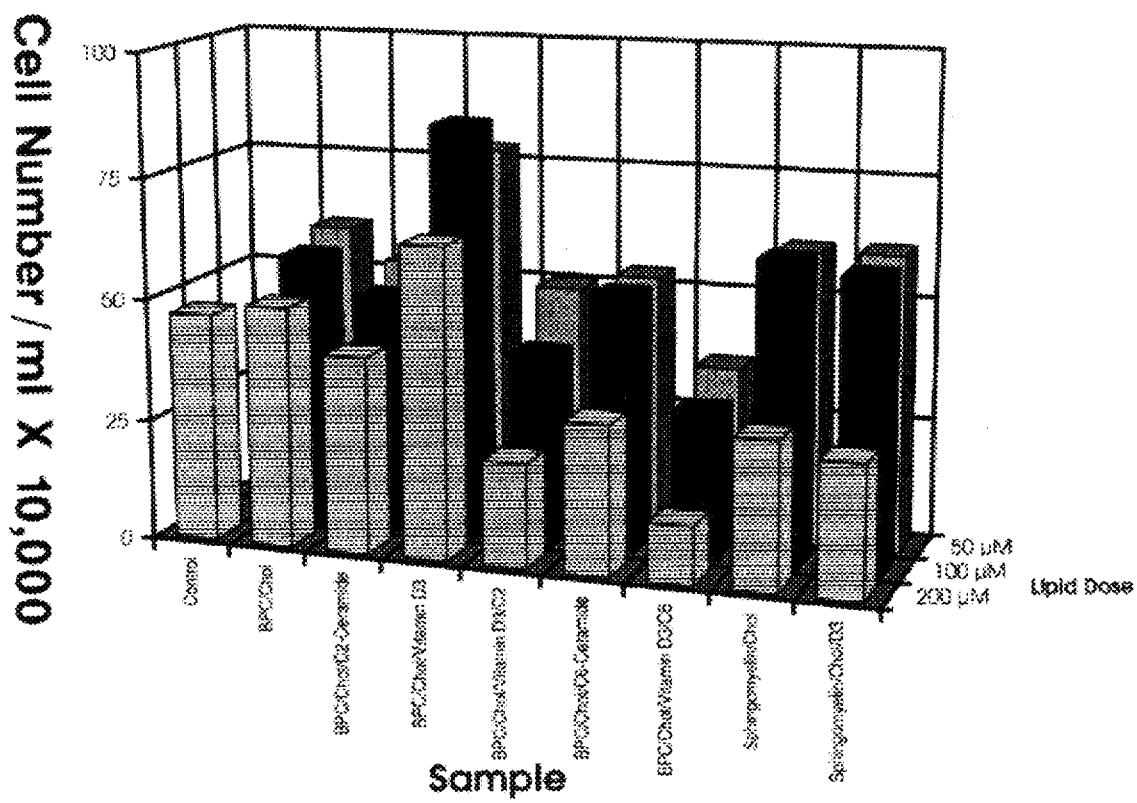
FIG. 4. Effect of Various Liposomal Ceramide/Sphingomyelin Formulations on the Growth of P388 Cells: The number of viable cells (per ml×10,000, y-axis) was determined for lipid doses of 50 μM, 100 μM and 200 μM (z-axis). X-axis: control, egg phosphatidylcholine/cholesterol (EPC/Chol), EPC/Chol/C2-ceramide (C2), EPC/Chol/vitamin D3 (D3), EPC/Chol/D3/C2, EPC/Chol/C6- ceramide (C6), EPC/Chol/D3/C6, Sphingomyelin (SM)/Chol and SM/Chol/D3 liposomes.

Effect of Various Liposomal Ceramide/ Sphingomyelin Formulations on the Growth of P388 Cells $2 \times 10^5$ P388 cells were incubated with various ceramide or sphingomyelin liposomal formulations (see Example 2, above), as well as with buffer alone and with egg phosphatidylcholine/cholesterol (EPC/Chol) liposomes, under the conditions given above. The number of viable cells in the cultures was determined for lipid doses of 50 µM, 100 µM and 200 µM. Results are reported in FIG. 4 and Tables 2 and 3.

Example 4

Effect of Various Liposomal Ceramide/ Sphingomyelin Formulations on the Growth of U937 Cells $2 \times 10^5$ U937 cells were incubated with the various ceramide or sphingomyelin liposomal formulations indicated above (see Example 2), as well as with buffer alone and with egg phosphatidylcholine/cholesterol (EPC/Chol) liposomes, under the conditions given above. The number of viable cells in the cultures was determined for lipid doses of 50 µM, 100 µM and 200 µM. Results are reported in FIGS. 5 and 7, and Tables 2 and 3.

Example 5

Effect of Various Liposomal Ceramide/ Sphingomyelin Formulations on the Growth of RPMI-7666 Cells $2 \times 10^5$ RPMI-7666 cells were incubated with the various ceramide/sphingomyelin liposomal formulations indicated above (see example 2), as well as with no liposomes (control) and with egg phosphatidylcholine/cholesterol (EPC/Chol) liposomes, under the conditions indicated above. The number of viable cells in the cultures was determined. Results are reported in FIGS. 6 and 7, and Tables 2 and 3.

Example 6

Effect of Various Liposomal Ceramide/ Sphingomyelin Formulations on the Growth of CHO/K1 Cells $2 \times 10^5$ CHO/k1 cells were incubated with the various ceramide/sphingomyelin liposomal formulations indicated above (see example 2), as well as with no liposomes (control) and with egg phosphatidylcholine/cholesterol (EPC/Chol) liposomes, under the conditions indicated above. The number of viable cells in the cultures was determined. Results are reported in Table 2.

TABLE 2

Survival of Various Cancer Lines (Without Serum)
% Survival (By trypan blue exclusion assay)

| Formulations | RPMI-7666 | U-937 | P-388 | HL-60 | CHO/k1 |
|---|---|---|---|---|---|
| BPC/CHOL/VD3 | 129.7, 107.1 | 113.4, 130 | 136, 103 | 87 | 138 |
| Control | 100 | 100 | 100 | 100 | 100 |
| BPC/CHOL/VD3/C-6 | 103, 90 | 63.5, 55 | 49.6, 26 | 37 | 73 |
| FREE C-6 CERAMIDE | 79 | 82.6 | 55.4 | — | — |
| FREE C6 m-silyl-ester | 85.6 | 80.6 | — | — | — |
| BPC/CHOL/VD3/C-2 | 93.7 | 49 | 46 | 47 | 90 |

Bioactive lipid dose = 20 uM

TABLE 3

Effect of Free and Liposomal ceramide on various cancer lines (With serum)
% Survival (By trypan blue assay)

| Formulations | RPMI-7666 | U-937 | P-388 |
|---|---|---|---|
| Control | 100 | 100 | 100 |
| BPC/CHOL/VD3/C-6 | 93.8 | 84.3 | 55.0 |
|  | 82 (thy)* | 75.1 (thy)* | 84.7 (thy)* |
| FREE C-6 CERAMIDE | 89.2 | 97 | 84.5 |

Bioactive lipid dose = 20 uM;*: growth inhibition measured by standard thymidine incorporation assay.

Example 7

Therapeutic Efficacy of Liposomal Ceramides in Mice

CDF1 mice were each injected intraperitoneally with $2.5 \times 10^6$ P388 cells. Groups having ten mice each were intraperitoneally administered either a HEPES-buffered saline control (10 mM HEPES, 150 mM NaCl, pH 7.4), or liposomal vitamin D3, liposomes containing C2 ceramide or liposomes containing C6 ceramide, prepared in accordance with the procedures described in Example 1 (see above), at a lipid dose of 1.5 mg of lipid per kg of body weight of the mice, the administration being 24 hours administration of the p388 cells. Survival was assessed at various times post-liposome/control administration. Results are presented in FIG. 8.

Example 8

In Vitro Cytoxicity Studies

These studies were performed using a sulforrhodamine B assay (see Monks et al., J. Natl. Cancer Inst. (U.S.) 83: 757 (1987)). Compounds were dissolved in ethanol. Results from these studies, presented in the following tables, are expressed as $GI_{50}$ values, that is, concentration of a drug (micromolar) required to inhibit growth of fifty percent of the cells.

TABLE 4

In Vitro Drug Sensitivity of Human and Mouse Cell Lines to Ceramide Derivatives
72 Hour Drug Exposure [$GI_{50}$ (uM) ± SD]

| Ceramide and derivatives | C6-Ceramide | 1-Acetate C6-Ceramide | 1,3-Diacetate C6-Ceramide | 1-Butyrate C6-Ceramide | 1-Isobutyrate C6-Ceramide |
|---|---|---|---|---|---|
| A549 | 12.0 ± 4.8 | 12.7 ± 7.6 | 6.1 ± 1.1 | 6.2 ± 0.4 | 7.9 ± 3.5 |
| MCF7 | 24.2 ± 8.5 | ND | 15.5 ± 0.2 | 17.9 ± 10.0 | ND |
| MCF7/ADR | 36.025 ± 0.88 | ND | 42.89 ± 3.6 | 37.80 ± 8.06 | 37.80 ± 4.67 |
| RPMI 7666 | 8.5 ± 3.5 | 9.0 ± 2.0 | ND | ND | ND |
| U937 | 7.0 ± 1.7 | 11.3 ± 1.0 | ND | ND | ND |
| LEWIS LUNG | 9.6 ± 4.4 | 8.5 ± 0.4 | 4.9 ± 0.5 | 6.4 ± 2.4 | ND |

ND — Not Done; *One Experiment Only

TABLE 5

In Vitro Drug Sensitivity of Human and Mouse Cell Lines to Ceramide Derivatives
72 Hour Drug Exposure [$GI_{50}$ (uM) ± SD]

| Ceramide and Derivatives | C6-Ceramide | 1-TBDMS C6-Ceramide | 3-TBDMS C6-Ceramide | 1,3-DiTBDMS C6-Ceramide | 1-TBDMS-3-Butyrate C6-Cer |
|---|---|---|---|---|---|
| A549 | 12.0 ± 4.8 | >200* | >200* | >200 | >200* |
| RPMI 7666 | 8.5 ± 3.5 | >200* | >200* | >200 | >200* |
| U937 | 7.0 ± 1.7 | >200* | >200* | 134.5 ± 28.8 | >200* |
| C3H10T1/2 | 14.0 ± 2.5 | >161.2* | >200* | ND | >200* |
| LEWIS LUNG | 9.6 ± 4.4 | >200* | >200* | >200 | >200* |

ND — Not Done; *One Experiment Only

TABLE 6

In Vitro Drug Sensitivity of Human and Mouse Cell Lines to Ceramide Derivatives
72 Hour Drug Exposure [$GI_{50}$ (uM) ± SD]

| Ceramide and Derivatives | C6-Ceramide | Sphingosine | N-Hexyl Sphingosine | 1-Acetate-3-one C6-Cer | 4,5-Diol C6-Ceramide |
|---|---|---|---|---|---|
| A549 | 12.0 ± 4.8 | 20.2 ± 0.8* | 4.9 ± 0.1 | 14.4 ± 0.1 | 25.1 ± 0.3* |
| MCF7 | 24.2 ± 8.5 | 20.4 ± 0.4* | 4.8 ± 0.1 | 6.7 ± 0.1 | 20.7 ± 0.1* |
| MCF7/ADR | 36.03 ± 0.88 | 19.8 ± 0.0* | 5.57 ± 1.17 | 14.7 ± 0.1* | 28.3 ± 1.1* |
| CAKI 1 | 6.04 ± 0.23 | 39.7 ± 0.8* | 6.84 ± 3.62 | ND | ND |
| OVCAR 3 | 15.15 ± 1.77 | 44.6 ± 0.9* | 4.99 ± 0.05* | 15.3 ± 0.1* | 38.2 ± 2.3* |
| HT 29 | 4.0 ± 0.2 | 19.3 ± 0.1* | 5.2 ± 0.1* | 13.9 ± 0.2* | 14.6 ± 0.4* |
| SKMEL 28 | 13.3 ± 2.51 | 15.6 ± 1.0* | 4.94 ± 0.66* | ND | ND |
| P388 | 6.24 ± 0.3 | ND | 2.59 ± 0.3* | ND | ND |
| P388/ADR | 12.7 ± 1.7* | ND | 2.61 ± 1.7* | ND | ND |
| LEWIS LUNG | 9.6 ± 4.4 | 12.2 ± 0.1 | 4.9 ± 0.1 | 14.5 ± 0.1 | 15.2 ± 0.1 |

ND = Not Done; *One Experiment Only

TABLE 7

In Vitro Drug Sensitivity of Selected Sphingosine Derivatives on a Diverse Tumor Cell Line Panel
72 Hour Drug Exposure

| Cell Lines | N-C4 Sphingosine | N-C6 Sphingosine | N-C8 Sphingosine | N-C8 Sphingosine HCl Salt | N-C10 Sphingosine | Cer-C6 |
|---|---|---|---|---|---|---|
| A549 | 4.90 +/− 0.10 | 4.90 +/− 0.06 | 4.91 +/− 0.01 | 4.97 +/− 0.19 | 4.99 +/− 0.08 | 8.08 +/− 0.06 |
| MCF 7 | 4.68 +/− 0.03 | 4.74 +/− 0.09 | 4.88 +/− 0.11 | 4.90 +/− 0.02 | 5.13 +/− 0.01 | 12.70 +/− 0.14 |
| MCF 7/ADR | 9.00 +/− 0.47 | 4.89 +/− 0.10 | 4.88 +/− 0.04 | 4.82 +/− 0.18 | 6.19 +/− 0.43 | 28.1 +/− 0.85 |
| OVCAR 3 | 14.05 +/− 0.35 | 4.99 +/− 0.05 | 5.41 +/− 0.13 | 5.23 +/− 0.01 | 12.50 +/− 0.85 | 15.15 +/− 1.77 |
| CAKI 1 | 6.88 +/− 0.52 | 4.28 +/− 0.04 | 4.64 +/− 0.07 | 4.47 +/− 0.01 | 6.18 +/− 0.01 | 5.88 +/− 0.10 |
| SKMEL 28 | 6.13 +/− 1.03 | 4.94 +/− 0.06 | 4.96 +/− 0.03 | 4.95 +/− 0.02 | 13.00 +/− 0.00 | 11.55 +/− 0.07 |
| HT 29 | 6.49 +/− 0.11 | 5.03 +/− 0.06 | 5.72 +/− 0.24 | 5.78 +/− 0.00 | 14.50 +/− 0.14 | 4.67 +/− 0.19 |
| LEWIS LUNG | 5.08 +/− 0.13 | 4.61 +/− 0.04 | 5.05 +/− 0.02 | 4.82 +/− 0.16 | 6.71 +/− 1.04 | 5.81 +/− 0.31 |

$GI_{50}$ (uM) +/− SD

TABLE 8

In Vitro Sensitivity of A549 and MCF 7/ADR to C6-Ceramide Derivatives at Different Drug Exposure Times
72 Hour Post-Drug Addition Incubation

| Drug Exposure Time | A549 | | | | MCF 7/ADR | | | |
|---|---|---|---|---|---|---|---|---|
| | 1-Acetate C6-Ceramide | 1-Butyrate C6-Ceramide | 1-Isobutyrate C6-Ceramide | N-C8 Sphingosine | 1-Acetate C6-Ceramide | 1-Butyrate C6-Ceramide | 1-Isobutyrate C6-Ceramide | N-C8 Sphingosine |
| 1 Hour Pulse | 92.9 +/− 1.3 | >100 | >100 | 31.2 +/− 5.0 | >100 | >100 | >100 | 34.3 +/− 4.2 |
| 4 Hour Pulse | 44.1 +/− 1.3 | 52.9 +/− 2.5 | >100 | 12.8 +/− 1.0 | 59.5 +/− 1.4 | 79.1 +/− 5.3 | >100 | 14.2 +/− 1.2 |
| 8 Hour Pulse | 35.3 +/− 2.5 | 36.5 +/− 0.8 | 40.2 +/− 2.5 | 6.7 +/− 0.2 | 42.7 +/− 1.2 | 44.0 +/− 1.1 | 52.3 +/− 1.6 | 8.9 +/− 0.2 |
| 24 Hour Pulse | 7.2 +/− 0.2 | 8.6 +/− 0.6 | 8.4 +/− 0.7 | 5.0 +/− 0.1 | 19.5 +/− 0.8 | 20.8 +/− 1.8 | 22.7 +/− 1.1 | 4.8 +/− 0.1 |
| 48 Hour Pulse | 4.35 +/− 0.1 | 4.7 +/− 0.1 | 5.2 +/− 0.3 | 4.8 +/− 0.1 | 15.6 +/− 0.9 | 17.2 +/− 0.1 | 18.7 +/− 0.5 | 4.62 +/− 0.1 |
| 72 Hour Continuous Exposure | 5.1 +/− 0.1 | 5.5 +/− 0.2 | 5.6 +/− 0.2 | 5.0 +/− 0.3 | 16.7 +/− 1.7 | 18.5 +/− 0.4 | 19.6 +/− 1.0 | 5.0 +/− 0.1 |

$GI_{50}$ (uM) +/− SD

Example 9

In Vivo Toxicity Studies

These studies were performed by intravenous injection of n-hexyl sphingosine, at the indicated dose (see below), into mice. Results are presented below.

TABLE 9

Toxicity of N-hexyl sphingosine after i.v injection in mice

| Dose (mg/kg) | Number of Animals Dead |
|---|---|
| Control (Tween-80) | 0/2 |
| 100 | 2/2 |
| 50 | 0/2* |
| 25 | 0/2** |
| 12.5 | 0/2 |

*Immediate ataxia, decreased activity. Respiration: Gasping.
After 30 minute decreased activity was still observed.
After 24 hours no abnormality was observed.
**Decrease activity immediately after injection.
After 30 minute no abnormality was observed.

Example 10

In Vivo Studies

These studies were performed using P-388/adriamycin resistant leukemia cells. Mice were injected i.p. with 100,000 cells, and then treated on days 1, 3 and 5 post-injection with n-hexyl sphingosine. Results are presented in FIG. 14.

Example 11

Compound Synthesis

Synthesis of sily ether of ceramide: The mixture of Ceramide and t-Butyldimethylsilyl chloride (1 equivalent) and imidazole (2 equivalent) in DMF was stirred under $N_2$ at room temperature overnight. The solvent was removed under a stream of $N_2$ and residue was dissolved in $CH_2Cl_2$, washed ($H_2O$), dried ($MgSO_4$) and concentrated to dryness. The residue was purified over silica gel (AcOEt:Hexan= 1:3).

Synthesis of 1-ester ceramide: The mixture of ceramide and Ac2O (1 equivalent) and catalytic amount of dimethyl amino pyridine in dry CH2Cl2 was stirred at room temperature for 1 hour and the reaction was checked by TLC (AcOEt). The mixture was concentrated. The crude product was purified over silica gel (AcOEt:Hexane=2:3.5).

Oxidation of C3-OH of ceramide to ketone: 1-OAc ceramide was dissolved in acetone and cooled in ice-bath. Jone's reagent was dropwised slowly till the orange color persistent. The reaction was quenched by isopropanol, and $NaHCO_3$ was added and stirred for 5 minutes. The solution was filtrate and concentrated to dryness. The crude product was purified by preparative TLC (ACOET:Hexane=1:2.5).

Reduction of ceramide to sphingosine analogs: To an ice-cold stirred solution of ceramide in anhydrous THF was added LiAlH$_4$ and the mixture was stirred at room temperature under N$_2$ for 24 hours. Under ice cooling the reaction mixtures was quenched by addition of saturated aqueous NaHCO$_3$. The resulting slurry was filtered and washed with THF. The solution was concentrated and the residue was brought into CH$_2$Cl$_2$, washed with H$_2$O, dried (MgSO$_4$) and concentrated to dryness. The residue was purified over preparative TLC (silica gel) CH2Cl2:MeOH:TEA=8:1:0.08.

Synthesis of 4,5-diol ceramide: To a solution of ceramide in a mixture of Me$_2$CO distilled H$_2$O and t-BuOH, N-Methyl morpholine N-oxide (NMO, 1.2 equivalent) and OsO$_4$ (catalytic amount) in THF were added. The reaction mixture was stirred at 45° C. for 6 hours and it was quenched by solid NaHCO$_3$ and the mixture was stirred for 15 minutes. The suspension was filtered and filtrate was dissolved in THF. The solution was washed with brine. The organic solution was separated, dried and concentrated to dryness. The residue was purified over preparative TLC (THF).

What is claimed is:

1. A liposome having a bilayer comprising a lipid component which comprises a compound having the formula R$^1$-Y$^1$—CHZ$^1$-CH(NY$^2$Y$^3$)—CH$_2$-Z$^2$, wherein:

R$^1$ is a straight-chained alkyl, alkenyl or alkynyl group having from 5 to 19 carbon atoms in the aliphatic chain;

Y$^1$ is —CH=CH—, —C≡C— or —CH(OH)CH(OH)—;

each of Z$^1$ and Z$^2$ is independently OH or a conversion-inhibiting group;

Y$^2$ is a phenyl group, an alkyl-substituted phenyl group having from 1 to about 6 carbons in the alkyl chain, or an alkyl chain having from 1 to 6 carbons;

Y$^3$ is H or a group having the formula —C(O)R$^2$ or —S(O)$_2$R$^2$;

R$^2$ is a straight-chained alkyl moiety selected from the group consisting of —(CH$_2$)$_3$CH$_3$, —(CH$_2$)$_5$CH$_3$, —(CH$_2$)$_7$CH$_3$ and —(CH$_2$)$_9$CH$_3$, or an alkenyl or alkynyl group having from 1 to 23 carbon atoms in the aliphatic chain;

Z$^2$ is a phosphorylcholine attachment-inhibiting group selected from the group consisting of -X$^1$, —OX$^1$, -X$^2$X$^3$ and —OX$^2$X$^3$;

X$^1$ is selected from the group consisting of —C(O)H, —CO$_2$H, CH$_3$(C(CH$_3$)$_3$)$_2$, Si(C(CH$_3$)$_3$)$_3$, Si(PO$_4$)$_2$C(CH$_3$)$_3$, a phenyl group, an alkyl-substituted phenyl group having from 1 to 6 carbons in the alkyl chain, an alkyl chain having from 1 to 6 carbons, an amino group, a fluorine, a chlorine, and a group having the formula C(R$^3$R$^4$)OH;

X$^2$ is selected from the group consisting of CH$_2$—, C(CH$_3$)$_2$—, Si(PO$_4$)$_2$—, Si(CH$_3$)$_2$—, SiCH$_3$PO$_4$—, C(O)— and S(O)$_2$—;

X$^3$ is selected from the group consisting of —C(O)H, —CO$_2$H, —CH$_3$, —C(CH$_3$)$_3$, —Si(CH$_3$)$_3$, —SiCH$_3$(C(CH$_3$)$_3$)$_2$, —Si(C(CH$_3$)$_3$)$_3$, —Si(PO$_4$)$_2$C(CH$_3$)$_3$, a phenyl group, an alkyl-substituted phenyl group having from 1 to 6 carbons in the alkyl chain, an alkyl chain having from 1 to 6 carbons, an amino moiety, a chlorine, a fluorine, or a group having the formula C(R$^3$R$^4$)OH, wherein each of R$^3$ and R$^4$ is independently an alkyl chain having from 1 to 6 carbons, a phenyl group or an alkyl-substituted phenyl group having from 1 to 6 carbons in the alkyl chain;

wherein when Z$^2$ is an amino group, R$^2$ is an aliphatic chain having from 1 to 9 or from 19 to 23 carbon atoms in the aliphatic chain, and wherein the compound comprises at least about 5 mole percent of the lipid.

2. The liposome of claim 1, wherein R$^1$ is CH$_3$(CH$_2$)$_{12}$—, Y$^1$ is —CH=CH— and Y$^2$ is H.

3. The liposome of claim 1, wherein Y$^3$ is —C(O)(CH$_2$)$_4$CH$_3$.

4. The liposome of claim 1, wherein the conversion-inhibiting group is —OSi(CH$_3$)$_2$C(CH$_3$)$_3$.

5. The liposome of claim 1, wherein the compound has the formula CH$_3$(CH$_2$)$_{12}$—CH=CH—CH$_2$Z$^1$-CH(NHY$^3$)—CH$_2$-Z$^2$.

6. The liposome of claim 5, wherein Y$^3$ is —C(O)(CH$_2$)$_4$CH$_3$ and wherein Z$^2$ is —OC(O)CH$_3$, —OC(O)CH$_2$CH$_2$CH$_3$, —OC(O)CH(CH$_3$)CH$_3$, or —OSi(CH$_3$)$_2$C(CH$_3$)$_3$.

7. The liposome of claim 1, wherein the compound comprises at least about 10 mole percent of the lipid.

8. The liposome of claim 1 comprising an additional bioactive agent.

9. The liposome of claim 1, wherein the lipid further comprises vitamin D$_3$.

10. The liposome of claim 9, wherein vitamin D$_3$ comprises about 1 mole percent of the lipid.

11. The liposome of claim 1, wherein the lipid further comprises a headgroup modified lipid.

12. The liposome of claim 1 which is dehydrated.

13. A pharmaceutical composition comprising the liposome of claim 1.

14. A method of administering a bioactive liposome to an animal which comprises administering to the animal the pharmaceutical composition of claim 13.

15. The method of claim 14, wherein the animal is afflicted with a cancer and wherein the amount of the composition administered comprises at least about 0.1 mg of the compound per kg of the animal's body weight.

* * * * *

UNITED STATES PATENT AND TRADEMARK OFFICE
CERTIFICATE OF CORRECTION

PATENT NO. : 5,681,589
DATED : October 28, 1997
INVENTOR(S) : Wei, et al.

It is certified that error appears in the above-identified patent and that said Letters Patent is hereby corrected as shown below:

On the title page, Item 54 and Col. 1:

Title, Line 2, change "LIPOSOMES" to --COMPOUNDS--.
Column 2, Line 8, change "apoptossis" to --apoptosis--.
Column 2, Line 14, change "Tumore Necrossis" to --Tumor Necrosis--.
Page 2, Column 1, Last line, change "insecsitive" to --insensitive--.
Page 2, Column 2, line 3, change "Phophonophingoglycolipid" to --Phosphonosphingoglycolipid--.
Column 1, Line 24, change "1993))" to --1993)--.
Column 2, Line 41, delete "()".
Column 5, Line 35, change "jour" to --hour--.
Column 7, Line 9, change "atached" to --attached--.
Column 13, Line 2, change "of sily" to --of a silyl--.
Column 13, Line 8, change "Hexan" to --Hexane--.
Column 13, Line 9, change "Ac2O" to --$Ac_2O$--.
Column 13, Line 11, change "CH2Cl2" to --$CH_2Cl_2$--.
Column 13, Line 42, change "meanns" to --means--.
Column 13, Line 49, change "sphingmyelin" to --sphingomyelin--.
Column 16, Line 9, change 'ampipathic" to --amphipathic--.
Column 24, Line 44 change "sily" to --silyl--.
Column 24, Line 51, change "Hexan" to --Hexane--.
Column 24, Line 54, change "Ac2O" to --$Ac_2O$--.
Column 24, Line 55, change "CH2Cl2" to --$CH_2Cl_2$--.

UNITED STATES PATENT AND TRADEMARK OFFICE
CERTIFICATE OF CORRECTION

PATENT NO. : 5,681,589
DATED : October 28, 1997
INVENTOR(S) : Wei, et al.

It is certified that error appears in the above-identified patent and that said Letters Patent is hereby corrected as shown below:

Column 24, Line 65, change "ACOET" to --AcOEt--.
Column 25, Line 8, change "CH2Cl2" to --$CH_2Cl_2$--.

Signed and Sealed this

First Day of September, 1998

BRUCE LEHMAN

Attesting Officer    Commissioner of Patents and Trademarks